(12) United States Patent
Schmalz et al.

(10) Patent No.: US 8,815,932 B2
(45) Date of Patent: Aug. 26, 2014

(54) INDUCTION OF ALPHA HELIX CONFORMATIONS IN PROTEINS AND PEPTIDES

(75) Inventors: Hans-Günther Schmalz, Brühl (DE); Ronald Kuhne, Berlin (DE); Verena Hack, Köln (DE); Cédric Reuter, Köln (DE)

(73) Assignees: Universität zu Köln, Köln (DE); Forschungsverbund Berlin E. V., Berlin (DE)

( * ) Notice: Subject to any disclaimer, the term of this patent is extended or adjusted under 35 U.S.C. 154(b) by 57 days.

(21) Appl. No.: 13/383,266

(22) PCT Filed: Jul. 9, 2010

(86) PCT No.: PCT/EP2010/004213
§ 371 (c)(1),
(2), (4) Date: Mar. 2, 2012

(87) PCT Pub. No.: WO2011/003626
PCT Pub. Date: Jan. 13, 2011

(65) Prior Publication Data
US 2012/0172402 A1 Jul. 5, 2012

(30) Foreign Application Priority Data
Jul. 10, 2009 (DE) .......... 10 2009 032 902

(51) Int. Cl.
C07D 487/18 (2006.01)
A61K 31/407 (2006.01)

(52) U.S. Cl.
USPC ......................... 514/411; 540/461

(58) Field of Classification Search
USPC .......................... 540/461; 514/411
See application file for complete search history.

(56) References Cited

U.S. PATENT DOCUMENTS

2003/0191049 A1 10/2003 Amblard et al.
2011/0034438 A1 2/2011 Kuehne

FOREIGN PATENT DOCUMENTS

EP 1 246 837 B1 10/2005
WO 2008/040332 A1 4/2008

OTHER PUBLICATIONS

Evans et al. (Tetrahedron Letters (1985), 26(16), 1911-14). Abstract.*
Kemp et al; "Studies of N-Terminal templates for alpha-helix formation. Synthesis and confirmational analysis of (2S, 5S, 8S, 11S)-1-Acetyl-1,4-diaza-3-keto-5-carboxy-10-thiatricyclo[2.8.1.0 4,8]-tridecane (Ac—Hel1—OH)"; J. Org. Chem. 1991, 56, pp. 6672-6682.
Zaminer et al; "Addressing protein-protein interactions with small molecules: a pro-pro dipeptide mimic with a PPII helix conformation as a module for the synthesis of PDR-binding ligands"; Angewandte Chemie Int. Ed. 2010, 49, pp. 7111-7115.
German Search Report dated Jun. 2, 2010.
Hack, et al; "Efficient α-helix induction in a linear peptide chain by N-capping with a bridged-tricyclic diproline analogue"; Agnew. Chem. Int. Ed. 2013, 52, 1-6.

* cited by examiner

*Primary Examiner* — Bruck Kifle
(74) *Attorney, Agent, or Firm* — Norris McLaughlin & Marcus, P.A.

(57) ABSTRACT

Substituted tricyclic diproline analogues of the formula (I):

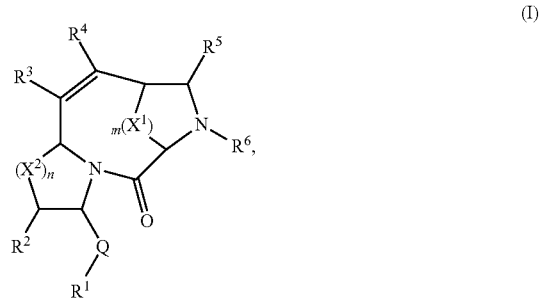

wherein the variables are as defined herein. Also disclosed are methods for the production thereof, the use thereof for the induction of an alpha-helix conformation in peptides and/or proteins, pharmaceuticals containing said compounds, methods for the production of a peptide library containing said compounds, and peptide libraries containing said compounds.

7 Claims, No Drawings

INDUCTION OF ALPHA HELIX CONFORMATIONS IN PROTEINS AND PEPTIDES

This application is a 371 of PCT/EP2010/004213, filed Jul. 9, 2010, which claims foreign priority benefit under 35 U.S.C. §119 of the German Patent Application No. 10 2009 032 902.1 filed Jul. 10, 2009, the disclosures of which are incorporated herein by reference.

The present invention relates to substituted tricyclic diproline derivatives, to processes for preparation thereof, to the use thereof for induction of an α-helix conformation in peptides and/or proteins, to medicaments comprising these compounds, to the use of these compounds for production of medicaments, to processes for production of peptide libraries comprising these compounds, and to peptide libraries comprising these compounds.

Peptides and proteins are essential constituents of organisms with a multitude of different functions. While the proteins assume biocatalytic tasks in particular (enzymes) and those as 10 important tissue constituents, the peptides fulfill important functions in the organism particularly as hormones, neurotransmitters and neuromodulators. Through binding to receptors (or to protein surfaces or protein complexes), peptides not only influence enzyme functions, but also specific macromolecular interactions (for example cell-cell communication or protein-protein interactions) and cell-physiological subsequent reactions mediated as a result. Thus, peptides control a multitude of vital processes such as metabolism, immune defense, digestion, respiration, sensation of pain, reproduction, behavior, electrolyte balance and others.

The interaction of peptide ligands with protein receptors plays an important role in the regulation of biological processes and depends crucially on the peptide geometry. Under physiological conditions, the conformation of a linear peptide, as a result of rotation about individual bonds, is in a dynamic equilibrium which depends on the pH and on the temperature. The effect of this is that the biological reactive conformation is present only in a low percentage.

The conformation of the peptide backbone is typically described by the three angles φ, ψ and ω. Due to the partial double bond character, the rotation of the peptide bond is hindered and it has a planar geometry, which leads to two preferential conformations: the trans and cis peptide bond with ω=180° and ω=0° respectively, the trans conformation being more energetically favorable and therefore predominant. Therefore, the torsion angles φ and ψ of the amino acid residues are sufficient in a first approximation to describe the conformation of the peptide backbone. The angle φ, which describes the rotation along the N—$C_\alpha$ bond, is defined by the four atoms C(=O)—N—$C_\alpha$C(=O). In the same way, N—$C_\alpha$C(=O)—N defines the angle ψ which describes the rotation about the $C_\alpha$C(=O) bond. Even though a large number of different combinations of φ and ψ is theoretically possible, there generally exist particular preferential conformations in peptides as a function of size, polarity and charge of the side chains, which leads to the formation of the known secondary structures such as α-helix, β-sheet, β-turn, etc.

WO 2008/040332 discloses compounds which can be used as mimetics for proline-containing peptides when they have a polyproline helix (PPII helix) conformation.

Such proline-containing proline-proline dipeptides, especially those with a PPII helix conformation, can function preferentially as ligands for what are called PRM binding domains (PRM=proline-rich motifs).

Proline, being the sole secondary amino acid among the 20 natural amino acids, as a result of the cyclization of the α-side chain on the amide nitrogen, has a torsion angle of φ=(−65±15°) as part of the five-membered ring, and is thus relatively restricted; the peptide consequently has fewer rotational degrees of freedom. One consequence of the double alkylation of the nitrogen is that the amide proton (in the peptide backbone) which is usually customary is absent, and proline is therefore not suitable as a hydrogen bond donor; secondly, the carbonyl group is particularly electron-rich and is therefore a better hydrogen bond acceptor than other amino acids. By virtue of these geometric and electronic properties, proline cannot stabilize an α-helix and also does not form a β-sheet structure, and is instead encountered in other typical secondary structures: what is called the β-turn and the polyproline helix (PPII helix).

Natural peptides are, however, often present in an α-helix conformation.

There is therefore a need for mimetics, especially for "proline-containing mimetics" (i.e. mimetics of proline-containing peptides), which are capable of exerting the function of receptor ligands and hence of modulating, i.e. of stimulating and/or inhibiting, the biological effects of a peptide and/or protein, and are present in an α-helix conformation.

It was therefore an object of the present invention to provide compounds which induce the formation of an α-helix conformation in such mimetics, preferably in proline-containing, more preferably in proline-rich mimetics, as a result of which these mimetics are capable of modulating, i.e. of stimulating and/or inhibiting, the biological effects of peptides and/or proteins present in α-helix conformation, i.e. exert an agonistic or antagonistic effect.

This object is achieved by the subject-matter of the claims.

It has now been found that, surprisingly, the substituted compounds of the general formula (I) specified below induce the formation of an α-helix conformation in peptides and/or proteins and are therefore especially suitable in medicaments for prophylaxis and/or treatment of disorders or diseases at least partly associated with the induction of an α-helix conformation in at least one protein and/or at least one peptide.

The invention provides substituted compounds of the general formula (I)

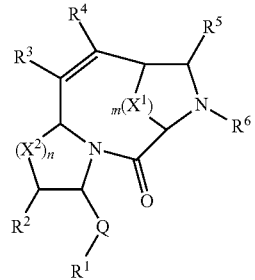

in which
Q is C(=O) or S(=O)$_2$;
$X^1$ and $X^2$ are each independently O, S, $CH_2$ or $CHR^7$,
  where $R^7$ is $C_{1-10}$-alkyl, saturated or unsaturated, branched or unbranched, unsubstituted or mono- or polysubstituted;
m is 1, 2 or 3;
n is 0, 1, 2 or 3;
$R^1$ is $C_{1-10}$-alkyl, saturated or unsaturated, branched or unbranched, unsubstituted or mono- or polysubstituted; $C_{2-10}$-cycloalkyl or heterocyclyl, each saturated or unsaturated, unsubstituted or mono- or polysubstituted; aryl or heteroaryl, each unsubstituted or mono- or polysubstituted; $C_{1-8}$-alkyl-bridged $C_{3-10}$-cycloalkyl or heterocyclyl, each saturated or unsaturated, unsubstituted or mono- or polysubstituted, where the alkyl chain in each case may be branched or unbranched, saturated or unsaturated, unsubstituted, mono- or polysubstituted; or $C_{1-8}$-alkyl-bridged aryl or heteroaryl, each unsubstituted or mono- or polysubstituted, where the alkyl chain in each case may be branched or unbranched, saturated or unsaturated, unsubstituted, mono- or polysubstituted; $OR^8$; $NR^8R^9$; $NHC(=O)R^8$; $NR^8R^9$; or $NH-S(=O)_2R^8$;

where $R^8$ and $R^9$ are each independently H; $C_{1-10}$-alkyl, saturated or unsaturated, branched or unbranched, unsubstituted or mono- or polysubstituted; $C_{3-10}$-cycloalkyl or heterocyclyl, each saturated or unsaturated, unsubstituted or mono- or polysubstituted; aryl or heteroaryl, each unsubstituted or mono- or polysubstituted; $C_{1-8}$-alkyl-bridged $C_{3-10}$-cycloalkyl or heterocyclyl, each saturated or unsaturated, unsubstituted or mono- or polysubstituted, where the alkyl chain in each case may be branched or unbranched, saturated or unsaturated, unsubstituted, mono- or polysubstituted; or $C_{1-8}$-alkyl-bridged aryl or heteroaryl, each unsubstituted or mono- or polysubstituted, where the alkyl chain in each case may be branched or unbranched, saturated or unsaturated, unsubstituted, mono- or polysubstituted;

or $R^1$ is $-NHCHR^aC(=O)-R^b$ where $R^a$ is selected from the group consisting of $-H$, $-CH_3$, $-CH(CH_3)_2$, $-CH_2CH(CH_3)_2$, $-CH(CH_3)CH_2CH_3$, $-CH_2CH_2SCH_3$, $-CH_2C_6H_5$, $-CH_2$-indolyl, $-CH_2OH$, $-CH(OH)CH_3$, $-CH_2C(=O)NH_2$, $CH_2CH_2C(=O)NH_2$, $-CH_2-C_6H_4-OH$, $-CH_2SH$, $-CH_2CH_2CH_2CH_2NH_2$, $-CH_2CH_2CH_2NHC(=NH)NH_2$, $-CH_2$-imidazolyl, $-CH_2CO_2H$, and $-CH_2CH_2CO_2H$; and $R^b$ is selected from $-OH$ and -peptidyl, where the peptidyl is bonded covalently via its N terminus;

$R^2$ and $R^5$ are each independently H; $C_{1-10}$-alkyl, saturated or unsaturated, branched or unbranched, unsubstituted or mono- or polysubstituted;

$R^3$ and $R^4$ are each independently H; $C_{1-10}$-alkyl, saturated or unsaturated, branched or unbranched, unsubstituted or mono- or polysubstituted; aryl or heteroaryl, each unsubstituted or mono- or polysubstituted;

$R^6$ is H; $C_{1-10}$-alkyl, saturated or unsaturated, branched or unbranched, unsubstituted or mono- or polysubstituted; $C_{3-10}$-cycloalkyl or heterocyclyl, each saturated or unsaturated, unsubstituted or mono- or polysubstituted; aryl or heteroaryl, each unsubstituted or mono- or polysubstituted; $C_{1-8}$-alkyl-bridged $C_{3-10}$-cycloalkyl or heterocyclyl, each saturated or unsaturated, unsubstituted or mono- or polysubstituted, where the alkyl chain in each case may be branched or unbranched, saturated or unsaturated, unsubstituted, mono- or polysubstituted; or $C_{1-8}$-alkyl-bridged aryl or heteroaryl, each unsubstituted or mono- or polysubstituted, where the alkyl chain in each case may be branched or unbranched, saturated or unsaturated, unsubstituted, mono- or polysubstituted; $C(=O)R^{10}$; $C(=O)OR^{10}$; $C(=O)NR^{10}R^{11}$; $S(=O)_2-R^{10}$; $S(=O)_2OR^{10}$; or $S(=O)_2NR^{10}R^{11}$;

where $R^{10}$ and $R^{11}$ are each independently H; $C_{1-10}$-alkyl, saturated or unsaturated, branched or unbranched, unsubstituted or mono- or polysubstituted; $C_{3-10}$-cycloalkyl or heterocyclyl, each saturated or unsaturated, unsubstituted or mono- or polysubstituted; aryl or heteroaryl, each unsubstituted or mono- or polysubstituted; $C_{1-8}$-alkyl-bridged $C_{3-10}$-cycloalkyl or heterocyclyl, each saturated or unsaturated, unsubstituted or mono- or polysubstituted, where the alkyl chain in each case may be branched or unbranched, saturated or unsaturated, unsubstituted, mono- or polysubstituted; or $C_{1-8}$-alkyl-bridged aryl or heteroaryl, each unsubstituted or mono- or polysubstituted, where the alkyl chain in each case may be branched or unbranched, saturated or unsaturated, unsubstituted, mono- or polysubstituted;

or $R^6$ is $-C(=O)-CHR^yNHR^z$ where $R^y$ is selected from the group consisting of $-H$, $-CH_3$, $-CH(CH_3)_2$, $-CH_2CH(CH_3)_2$, $-CH(CH_3)CH_2CH_3$, $-CH_2CH_2SCH_3$, $-CH_2C_6H_5$, $-CH_2$-indolyl, $-CH_2OH$, $-CH(OH)CH_3$, $-CH_2C(=O)NH_2$, $CH_2CH_2C(=O)NH_2$, $-CH_2-C_6H_4-OH$, $-CH_2SH$, $-CH_2CH_2CH_2CH_2NH_2$, $-CH_2CH_2CH_2NHC(=NH)NH_2$, $-CH_2$-imidazolyl, $-CH_2CO_2H$, and $-CH_2CH_2CO_2H$; and $R^z$ is selected from $-H$ and $-C(=O)-C_{1-8}$-alkyl;

in which "alkyl substituted", "heterocyclyl substituted" and "cycloalkyl substituted" on the corresponding radicals represents the substitution of one or more hydrogen atoms in each case independently by F; Cl; Br; I; $NO_2$; CN; $CF_3$; $C_{1-8}$-alkyl; phenyl; $C(=O)OH$; $C(=O)O-C_{1-8}$-alkyl; $C(=O)O$-phenyl; $C(=O)NH_2$; $C(=O)NH-C_{1-8}$-alkyl; $C(=O)NH$-phenyl; $C(=O)N(C_{1-8}$-alkyl$)_2$; OH; =O; $OCF_3$; $O-C_{1-8}$-alkyl; $O-C(=O)-C_{1-8}$-alkyl; SH; $SCF_3$; $S-C_{1-8}$-alkyl; $S(=O)_2OH$; $S(=O)_2C_{1-8}$-alkyl; $S(=O)_2O-C_{1-8}$-alkyl; $S(=O)_2NH-C_{1-8}$-alkyl; $S(=O)_2N(C_{1-8}$-alkyl$)_2$; $NH_2$; $NH-C_{1-8}$-alkyl; NH-phenyl; $N(C_{1-8}$-alkyl$)_2$; $NH-C(=O)-C_{1-8}$-alkyl; $NH-S(=O)_2-C_{1-8}$-alkyl;

in which "aryl substituted" and "heteroaryl substituted" on the corresponding radicals represents the substitution of one or more hydrogen atoms in each case independently by F; Cl; Br; I; $NO_2$; CN; $CF_3$; $C_{1-8}$-alkyl; phenyl; $C(=O)OH$; $C(=O)O-C_{1-8}$-alkyl; $C(=O)O$-phenyl; $C(=O)NH_2$; $C(=O)NH-C_{1-8}$-alkyl; $C(=O)NH$-phenyl; $C(=O)N(C_{1-8}$-alkyl$)_2$; OH; $OCF_3$; $O-C_{1-8}$-alkyl; $O-C(=O)-C_{1-8}$-alkyl; SH; $SCF_3$; $S-C_{1-8}$-alkyl; $S(=O)_2OH$; $S(=O)_2 C_{1-8}$-alkyl; $S(=O)_2O-C_{1-8}$-alkyl; $S(=O)_2NH-C_{1-8}$-alkyl; $S(=O)_2N(C_{1-8}$-alkyl$)_2$; $NH_2$; $NH-C_{1-8}$-alkyl; NH-phenyl; $N(C_{1-8}$-alkyl$)_2$; $NH-C(=O)-C_{1-8}$-alkyl; $NH-S(=O)_2-C_{1-8}$-alkyl;

in each case in the form of the free compounds; of the racemates; of the enantiomers, diastereomers, mixtures of the enantiomers or diastereomers, or of a single enantiomer or diastereomer; or in the form of the salts of physiologically compatible acids or bases; or if appropriate in the form of solvates.

"Peptidyl" in the context of the invention is understood to mean a peptide radical which comprises peptide-linked proteinogenic amino acid residues, preferably in L configuration, the total number of amino acid residues being preferably 1, 2, 3, 4, 5, 6, 7, 8, 9, 10, 11, 12, 13, 14, 15, 16, 17, 18, 19 or 20.

"Peptidyl" is preferably the following residue:
$-NR^{c'}-CHR^c-C(=O)-[NR^{d'}-CHR^d-C(=O)]_d-$
$[NR^{e'}-CHR^e-C(=O)]_e-[NR^{f'}-CHR^f-C(=O)]_f-$
$[NR^{g'}-CHR^g-C(=O)]_g-[NR^{h'}-CHR^h-C(=O)]_h-$
$[NR^{i'}-CHR^i-C(=O)]_i-[NR^{j'}-CHR^j-C(=O)]_j-$
$[NR^{k'}-CHR^k-C(=O)]_k-[NR^{l'}-CHR^l-C(=O)]_l-$
$[NR^{m'}-CHR^m-C(=O)]_m-[NR^{n'}-CHR^n-C(=O)]_n$
$-NR^{o'}-CHR^o-C(=O)]_o-[NR^{p'}-CHR^p-C(=O)]_p$
$-[NR^{q'}-CHR^q-C(=O)]_q-[NR^{r'}-CHR^r-C(=O)]_r$
$-NR^{s'}-CHR^s-C(=O)]_s-[NR^{t'}-CHR^t-C(=O)]_t-$
$[NR^{u'}-CHR^u-C(=O)]_u-[NR^{v'}-CHR^v-C(=O)]_v-$
OH, where
$R^c, R^d, R^e, R^f, R^g, R^h, R^i, R^j, R^k, R^l, R^m, R^n, R^o, R^p, R^q, R^r, R^s, R^t, R^u$ and $R^v$ are each independently selected from the group consisting of —H, —CH$_3$, —CH(CH$_3$)$_2$, —CH$_2$CH(CH$_3$)$_2$, —CH(CH$_3$)CH$_2$CH$_3$, —CH$_2$CH$_2$SCH$_3$, —CH$_2$C$_6$H$_5$, —CH$_2$-indolyl, —CH$_2$OH, —CH(OH)CH$_3$, —CH$_2$C(=O)NH$_2$, —CH$_2$CH$_2$C(=O)NH$_2$, —CH$_2$-C$_6$H$_4$—OH, —CH$_2$SH, —CH$_2$CH$_2$CH$_2$CH$_2$NH$_2$—CH$_2$CH$_2$CH$_2$NHC(=NH)NH$_2$, —CH$_2$-imidazolyl, —CH$_2$CO$_2$H, and —CH$_2$CH$_2$CO$_2$H;
$R^{c'}, R^{d'}, R^{e'}, R^{f'}, R^{g'}, R^{h'}, R^{i'}, R^{j'}, R^{k'}, R^{l'}, R^{m'}, R^{n'}, R^{o'}, R^{p'}, R^{q'}, R^{r'}, R^{s'}, R^{t'}, R^{u'}$ and $R^{v'}$ are each —H;
or
$R^c$ and $R^{c'}$, $R^d$ and $R^{d'}$, $R^e$ and $R^{e'}$, $R^f$ and $R^{f'}$, $R^g$ and $R^{g'}$, $R^h$ and $R^{h'}$, $R^i$ and $R^{i'}$, $R^j$ and $R^{j'}$, $R^k$ and $R^{k'}$, $R^l$ and $R^{l'}$, $R^m$ and $R^{m'}$, $R^n$ and $R^{n'}$, $R^o$ and $R^{o'}$, $R^p$, and $R^{p'}$, $R^q$ and $R^{q'}$, $R^r$ and $R^{r'}$, $R^s$ and $R^{s'}$, $R^t$ and $R^{t'}$, $R^u$ and $R^{u'}$ or $R^v$ and $R^{v'}$, in each case together are —CH$_2$CH$_2$CH$_2$— and form a five-membered ring; and
the indices d, e, f, g, h, i, j, k, l, m, n, o, p, q, r, s, t, u and v are each independently 0 or 1.

The expressions "alkyl", and "C$_{1-10}$-alkyl", "C$_{1-8}$-alkyl", "C$_{1-4}$-alkyl", encompass, in the context of this invention, acyclic saturated or unsaturated aliphatic hydrocarbyl radicals, i.e. C$_{1-10}$ aliphatic radicals, C$_{1-8}$ aliphatic radicals and C$_{1-4}$ aliphatic radicals, each of which may be branched or unbranched and unsubstituted or mono- or polysubstituted, having 1 to 10 or 1 to 8 or 1 to 4 carbon atoms, i.e. C$_{1-10}$-alkanyls, C$_{2-10}$-alkenyls and C$_{2-10}$-alkynyls, or C$_{1-8}$-alkanyls, C$_{2-8}$-alkenyls and C$_{2-8}$-alkynyls, or C$_{1-4}$-alkanyls, C$_{2-4}$-alkenyls and C$_{2-4}$-alkynyls. Alkenyls have at least one C—C double bond and alkynyls at least one C—C triple bond. Alkyl is preferably selected from the group comprising methyl, ethyl, n-propyl, 2-propyl, n-butyl, isobutyl, sec-butyl, tert-butyl, n-pentyl, isopentyl, neopentyl, n-hexyl, n-heptyl, n-octyl, n-nonyl, n-decyl, ethenyl (vinyl), ethynyl, propenyl (—CH$_2$CH=CH$_2$, —CH=CH—CH$_3$, —C(=CH$_2$)—CH$_3$), propynyl (—CH—C≡CH, —C≡C—CH$_3$), butenyl, butynyl, pentenyl, pentynyl, hexenyl and hexynyl, heptenyl, heptynyl, octenyl, octynyl, nonenyl, nonynyl, decenyl and decynyl.

The expressions "cycloalkyl" or "C$_{3-10}$-cycloalkyl" for the purposes of this invention mean cyclic aliphatic (cycloaliphatic) hydrocarbyl radicals having 3, 4, 5, 6, 7, 8, 9 or 10 carbon atoms, i.e. C$_{3-10}$ cycloaliphatic radicals, where the hydrocarbons may be saturated or unsaturated (but not aromatic), unsubstituted or mono- or polysubstituted. The cycloalkyl may be bonded to the respective general parent structure via any possible ring member of the cycloalkyl radical. The cycloalkyl radicals may also be fused to further saturated, (partially) unsaturated, (hetero)cyclic, aromatic or heteroaromatic ring systems, i.e. cycloalkyl, heterocyclyl, aryl or heteroaryl, which may in turn be unsubstituted or mono- or polysubstituted. The cycloalkyl radicals may also be singly or multiply bridged, as, for example, in the case of adamantyl, bicyclc[2.2.1]heptyl or bicycle[2.2.2]octyl. Cycloalkyl is preferably selected from the group comprising cyclopropyl, cyclobutyl, cyclopentyl, cyclohexyl, cycloheptyl, cyclooctyl, cyclononyl, cyclodecyl, adamantyl,

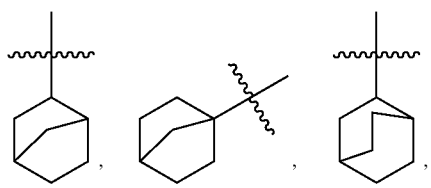

-continued

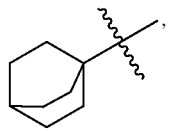

cyclopentenyl, cyclohexenyl, cycloheptenyl and cyclooctenyl.

The terms "heterocyclyl" and "heterocycloalkyl" encompass aliphatic saturated or unsaturated (but nonaromatic) cycloalkyls having three to ten, i.e. 3, 4, 5, 6, 7, 8, 9 or 10 ring members, in which at least one carbon atom, optionally also two or three carbon atoms, is/are replaced by a heteroatom or a heteroatom group in each case independently selected from the group consisting of O, S, S(=O)$_2$, N, NH and N(C$_{1-8}$-alkyl), preferably N(CH$_3$), where the ring members may be unsubstituted or mono- or polysubstituted. Heterocycles are thus heterocycloaliphatic radicals. The heterocyclyl may be bonded to the general parent structure via any possible ring member of the heterocyclyl radicals. The heterocyclyl radicals may also be fused to further saturated, (partially) unsaturated, (hetero)cyclic or aromatic or heteroaromatic ring systems, i.e. to cycloalkyl, heterocyclyl, aryl or heteroaryl, which may in turn be unsubstituted or mono- or polysubstituted. Preference is given to heterocyclyl radicals from the group comprising azetidinyl, aziridinyl, azepanyl, azocanyl, diazepanyl, dithiolanyl, dihydroquinolinyl, dihydropyrrolyl, dioxanyl, dioxolanyl, dioxepanyl, dihydroindenyl, dihydropyridinyl, dihydrofuranyl, dihydroisoquinolinyl, dihydroindolinyl, dihydro-isoindolyl, imidazolidinyl, isoxazolidinyl, morpholinyl, oxiranyl, oxetanyl, pyrrolidinyl, piperazinyl, 4-methylpiperazinyl, piperidinyl, pyrazolidinyl, pyranyl, tetrahydropyrrolyl, tetrahydropyranyl, tetrahydroquinolinyl, tetrahydro-isoquinolinyl, tetrahydroindolinyl, tetrahydrofuranyl, tetrahydropyridinyl, tetrahydrothiophenyl, tetrahydro-pyridoindolyl, tetrahydronaphthyl, tetrahydro-carbolinyl, tetrahydroisoxazolopyridinyl, thiazolidinyl and thiomorpholinyl.

The term "aryl" in the context of this invention means aromatic hydrocarbons having up to 14 ring members, including phenyls and naphthyls. Each aryl radical may be unsubstituted or mono- or polysubstituted, in which case the aryl substituents may be the same or different and may be in any possible position on the aryl. The aryl may be bonded to the general parent structure via any possible ring member of the aryl radical. The aryl radicals may also be fused to further saturated, (partially) unsaturated, (hetero)cyclic, aromatic or heteroaromatic ring systems, i.e. to cycloalkyl, heterocyclyl, aryl or heteroaryl, which may in turn be unsubstituted or mono- or polysubstituted. One example of a fused aryl radical is fluorenyl. Aryl is preferably selected from the group comprising phenyl, fluorenyl, 1-naphthyl and 2-naphthyl, each of which may be unsubstituted or mono- or polysubstituted. A particularly preferred aryl is phenyl, unsubstituted or mono- or polysubstituted.

The term "heteroaryl" represents a 5- or 6-membered cyclic aromatic radical which contains at least 1 heteroatom, optionally also 2, 3, 4 or 5 heteroatoms, where the heteroatoms are each independently selected from the group of S, N and O and the heteroaryl radial may be unsubstituted or mono- or polysubstituted; in the case of substitution on the heteroaryl, the substituents may be the same or different and may be in any possible position on the heteroaryl. The bonding to the general parent structure may be via any possible ring member of the heteroaryl radical. The heteroaryl may also be part of a bi- or polycyclic system having up to 14 ring members, and the ring system may be formed by further saturated, (partially) unsaturated, (hetero)cyclic or aromatic or heteroaromatic rings, i.e. with cycloalkyl, heterocyclyl, aryl or heteroaryl, which may in turn be unsubstituted or mono- or polysubstituted. It is preferable that the heteroaryl radical is selected from the group comprising benzofuranyl, benzimidazolyl, benzothienyl, benzothiadiazolyl, benzothiazolyl, benzotriazolyl, benzoxazolyl, benzoxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazolyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, tetrazol, thienyl (thiophenyl), triazolyl, tetrazolyl, triazolyl, thiadiazolyl or triazinyl. Particular preference is given to pyridyl and thienyl.

The expressions "aryl, heteroaryl, heterocyclyl or cycloalkyl bridged via $C_{1-4}$-alkyl or $C_{1-8}$-alkyl" mean, in the context of the invention, that $C_{1-4}$-alkyl or $C_{1-8}$-alkyl and aryl or heteroaryl or heterocyclyl or cycloalkyl are each as defined above, and the aryl or heteroaryl or heterocyclyl or cycloalkyl radical is bonded to the general parent structure via a $C_{1-4}$-alkyl or a $C_{1-8}$-alkyl group. The alkyl chain of the alkyl group may in all cases be branched or unbranched, unsubstituted or mono- or polysubstituted. The alkyl chain of the alkyl group may also in all cases be saturated or unsaturated, i.e. may be an alkylene group, i.e. a $C_{1-4}$-alkylene group or a $C_{1-8}$-alkylene group, an alkenylene group, i.e. a $C_{2-4}$-alkenylene group or a $C_{2-8}$-alkenylene group, or an alkynylene group, i.e. a $C_{2-4}$-alkynylene group or a $C_{2-8}$-alkynylene group. $C_{1-4}$-alkyl is preferably selected from the group comprising —$CH_2$—, —$CH_2$—$CH_2$—, —$CH(CH_3)$—, —$CH_2$—$CH_2$—$CH_2$—, —$CH(CH_3)$—$CH_2$—, —$CH(CH_2CH_3)$—, —$CH_2$—$(CH_2)_2$—$CH_2$—, —$CH(CH_3)$—$CH_2$—$CH_2$—, —$CH_2$—$CH(CH_3)$—$CH_2$—, —$CH(CH_3)$—$CH(CH_3)$—, —$CH(CH_2CH_3)$—$CH_2$—, —$C(CH_3)_2$—$CH_2$—, —$CH(CH_2CH_2CH_3)$—, —$C(CH_3)(CH_2CH_3)$—, —$CH$=$CH$—, —$CH$=$CH$—$CH_2$—, —$C(CH_3)$=$CH_2$—, —$CH$=$CH$—$CH_2$—$CH_2$—, —$CH_2$—$CH$=$CH$—$CH_2$—, —$CH$=$CH$—$CH$=$CH$—, —$C(CH_3)$=$CH$—$CH_2$—, —$CH$=$C(CH_3)$—$CH_2$—, —$C(CH_3)$=$C(CH_3)$—, —$C(CH_2CH_3)$=$CH$—, —$C$≡$C$—, —$C$≡$C$—$CH_2$—, —$C$≡$C$—$CH_2$—$CH_2$—, —$C$≡$C$—$CH(CH_3)$—, —$CH_2$—$C$≡$C$—$CH_2$— and —$C$≡$C$—$C$≡$C$— and $C_{1-8}$-alkyl selected from the group comprising —$CH_2$—, —$CH_2$—$CH_2$—, —$CH(CH_3)$—, —$CH_2$—$CH_2$—$CH_2$—, —$CH(CH_3)$—$CH_2$—, —$CH(CH_2CH_3)$—, —$CH_2$—$(CH_2)_2$—$CH_2$—, —$CH(CH_3)$—$CH_2$—$CH_2$—, —$CH_2$—$CH(CH_3)$—$CH_2$—, —$CH(CH_3)$—$CH(CH_3)$—, —$CH(CH_2CH_3)$—$CH_2$—, —$C(CH_3)_2$—$CH_2$—, —$CH(CH_2CH_2CH_3)$—, —$C(CH_3)(CH_2CH_3)$—, —$CH_2$—$(CH_2)_3$—$CH_2$—, —$CH(CH_3)$—$CH_2$—$CH_2$—$CH_2$—, —$CH_2$—$CH(CH_3)$—$CH_2$—$CH_2$—, —$CH(CH_3)$—$CH_2$—$CH(CH_3)$—, —$CH(CH_3)$—$CH(CH_3)$—$CH_2$—, —$C(CH_3)_2$—$CH_2$—$CH_2$—, —$CH_2$—$C(CH_3)_2$—$CH_2$—, —$CH(CH_2CH_3)$—$CH_2$—$CH_2$—, —$CH_2$—$CH(CH_2CH_3)$—$CH_2$—, —$C(CH_3)_2$—$CH(CH_3)$—, —$CH(CH_2CH_3)$—$CH(CH_3)$—, —$C(CH_3)(CH_2CH_3)$—$CH_2$—, —$CH(CH_2CH_2CH_3)$—$CH_2$—, —$C(CH_2CH_2CH_3)$—$CH_2$—, —$CH(CH_2CH_2CH_2CH_3)$—, —$C(CH_3)(CH_2CH_2CH_3)$—, —$C(CH_2CH_3)_2$—, —$CH_2$—$(CH_2)_4$—$CH_2$—, —$CH$=$CH$—, —$CH$=$CH$—$CH_2$—, —$C(CH_3)$=$CH_2$—, —$CH$=$CH$—$CH_2$—$CH_2$—, —$CH_2$—$CH$=$CH$—$CH_2$—, —$CH$=$CH$—$CH$=$CH$—, —$C(CH_3)$=$CH$—$CH_2$—, —$CH$=$C(CH_3)$—$CH_2$—, —$C(CH_3)$=$C(CH_3)$—, —$C(CH_2CH_3)$=$CH$—, —$CH$=$CH$—$CH_2$—$CH_2$—$CH_2$—, —$CH_2$—$CH$=$CH$—$CH_2$—$CH_2$—$CH_2$—, —$CH$=$CH$—$CH_2$—$CH_2$—, —$CH$=$CH_2$—$CH$=$CH_2$—, —$CH_2$—, —$C$≡$C$—, —$C$≡$C$—$CH_2$—, —$C$≡$C$—$CH(CH_3)$—, —$CH_2$—$CH_2$—, —$C$≡$C$—, —$C$≡$C$—$CH_2$—, —$C$≡$C$—$CH_2$—$CH_2$—, —$C$≡$C$—$CH(CH_3)$—, —$CH_2$—$CH_2$—, —$C$≡$C$—$C(CH_3)$—, —$CH_2$—$C$≡$C$—$CH_2$—, —$C$≡$C$—$C$≡$C$—$CH_2$—, —$C$≡$C$—$C$≡$C$—$CH_2$—, —$C$≡$C$—$C(CH_3)_2$—, —$C$≡$C$—$CH_2$—$CH_2$—$CH_2$—, —$CH_2$—$C$≡$C$—$CH_2$—$CH_2$—, —$C$≡$C$—$C$≡$C$—$CH_2$— and —$C$≡$C$—$CH_2$—$C$≡$C$—.

In connection with "alkyl", "heterocyclyl" and "cycloalkyl", the term "mono- or polysubstituted" is understood in the context of this invention to mean the single or multiple, for example double, triple or quadruple, substitution of one or more hydrogen atoms each independently by substituents selected from the group of F; Cl; Br; I; $NO_2$; CN; $CF_3$; $C_{1-8}$-alkyl; phenyl; C(=O)OH; C(=O)O—$C_{1-8}$-alkyl; C(=O)O-phenyl; C(=O)$NH_2$; C(=O)NH—$C_{1-8}$-alkyl; C(=O)NH-phenyl; C(=O)N($C_{1-8}$-alkyl)$_2$; OH; =O; $OCF_3$; O—$C_{1-8}$-alkyl; O—C(=O)—$C_{1-8}$-alkyl; SH; $SCF_3$; S—$C_{1-8}$-alkyl; S(=O)$_2$OH; S(=O)$_2C_{1-8}$-alkyl; S(=O)$_2$O—$C_{1-8}$-alkyl; S(=O)$_2$NH—$C_{1-8}$-alkyl; S(=O)$_2$N($C_{1-8}$-alkyl)$_2$; $NH_2$; NH—$C_{1-8}$-alkyl; NH-phenyl; N($C_{1-8}$-alkyl)$_2$; NH—C(=O)—$C_{1-8}$-alkyl; NH—S(=O)$_2$—$C_{1-8}$-alkyl; where polysubstituted radicals are understood to mean those radicals which are polysubstituted, e.g. di-, tri- or tetrasubstituted, either on different or the same atoms, for example trisubstituted on the same carbon atom as in the case of $CF_3$ or $CH_2CF_3$, or at different positions as in the case of CH(OH)—CH=CH—$CHCl_2$. A substituent may optionally itself in turn be mono- or polysubstituted. Polysubstitution can be effected with the same substituent or with different substituents.

Preferred "alkyl", "heterocyclyl" and "cycloalkyl" substituents are selected from the group of by of F, Cl, Br, I, $C_{1-4}$-alkyl, C(=O)OH, C(=O)O$C_{1-4}$-alkyl, C(=O)$C_{1-4}$-alkyl, C(=O)NH—$C_{1-4}$-alkyl, OH, O—$C_{1-4}$-alkyl, =O, $NH_2$, NHC(=O)$C_{1-4}$-alkyl, NHS(=O)$_2C_{1-4}$-alkyl, S(=O)$_2$OH, S(=O)$_2$O$C_{1-4}$-alkyl and S(=O)$_2C_{1-4}$-alkyl.

In connection with "aryl" and "heteroaryl", "mono- or polysubstituted" is understood in the context of this invention to mean the mono- or polysubstitution, e.g. di-, tri- or tetrasubstitution, of one or more hydrogen atoms of the ring system each independently by substituents selected from the group of F; Cl; Br; I; $NO_2$; CN; $CF_3$; $C_{1-8}$-alkyl; phenyl; C(=O)OH; C(=O)O—$C_{1-8}$-alkyl; C(=O)O-phenyl; C(=O)$NH_2$; C(=O)NH—$C_{1-8}$-alkyl; C(=O)NH-phenyl; C(=O)N($C_{1-8}$-alkyl)$_2$; OH; $OCF_3$; O—$C_{1-8}$-alkyl; O—C(=O)—$C_{1-8}$-alkyl; SH; $SCF_3$; S—$C_{1-8}$-alkyl; S(=O)$_2$OH; S(=O)$_2C_{1-8}$-alkyl; S(=O)$_2$O—$C_{1-8}$-alkyl; S(=O)$_2$NH—$C_{1-8}$-alkyl; S(=O)$_2$N($C_{1-8}$-alkyl)$_2$; $NH_2$; NH—$C_{1-8}$-alkyl; NH-phenyl; N($C_{1-8}$-alkyl)$_2$; NH—C(=O)—$C_{1-8}$-alkyl; NH—S(=O)$_2$—$C_{1-8}$-alkyl; on one or, if appropriate, different atoms, where a substituent may optionally itself in turn be mono- or polysubstituted. Polysubstitution is effected with the same substituent or with different substituents.

Preferred "aryl" and "heteroaryl" substituents are selected from the group consisting of F, Cl, Br, I, $C_{1-4}$-alkyl, C(=O)OH, C(=O)O$C_{1-4}$-alkyl, C(=O)$C_{1-4}$-alkyl, C(=O)NH—$C_{1-4}$-alkyl, OH, O—$C_{1-4}$-alkyl, $NH_2$, NHC(=O)$C_{1-4}$-alkyl, NHS(=O)$_2C_{1-4}$-alkyl, S(=O)$_2$OH, S(=O)$_2$O$C_{1-4}$-alkyl and S(=O)$_2C_{1-4}$-alkyl.

The compounds of the general formula (I) are defined by substituents, for example by $R^1$, $R^2$ and $R^3$ (1st generation substituents) which are themselves optionally substituted (2nd generation substituents). According to the definition, these substituents of the substituents may themselves again be substituted (3rd generation substituents). If, for example, $R^1$=aryl (1st generation substituent), aryl may itself be substituted, for example by $C_{1-8}$-alkyl (2nd generation substituent). The result is the functional group aryl-$C_{1-8}$-alkyl. $C_{1-8}$-Alkyl may then itself again be substituted, for example by Cl (3rd generation substituent). The overall result is then the functional group aryl-$C_{1-8}$-alkyl-Cl.

In a preferred embodiment, the 3rd generation substituents, however, cannot be substituted again, i.e. there are then no 4th generation substituents.

In another preferred embodiment, the 2nd generation substituents cannot be substituted again, i.e. there are then no 3rd generation substituents. In other words, in this embodiment, for example in the case of the general formula (I), functional groups for $R^1$ to $R^{11}$ may each optionally be substituted, but the respective substituents may then themselves not be substituted again.

In the context of the present invention, the symbol used in the formulae

denotes a linkage of a corresponding radical to the respective general parent structure.

When a radical occurs more than once within a molecule, for example the $R^7$ radical, this radical may have different meanings in each case for different substituents: when, for example, both $X^1$=$CHR^7$ and $X^2$=$CHR^7$, $R^7$ for $X^1$ may be H and $R^7$ for $X^2$ may be $C_{1-10}$-alkyl.

The term "salt formed with a physiologically acceptable acid" is understood in the context of this invention to mean salts of the respective active ingredient with inorganic or organic acids which are physiologically acceptable—especially in the case of use in humans and/or mammals. Particular preference is given to the hydrochloride. Examples of physiologically acceptable acids are: hydrochloric acid, hydrobromic acid, sulfuric acid, methanesulfonic acid, p-toluenesulfonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, hippuric acid, phosphoric acid, aspartic acid. Particular preference is given to citric acid and hydrochloric acid.

Physiologically acceptable salts with cations or bases are salts of the respective compound—as the anion with at least one preferably inorganic cation—which are physiologically acceptable—especially in the case of use in humans and/or mammals. Particular preference is given to the salts of the alkali metals and alkaline earth metals, but also ammonium salts $[NH_xR_{4-x}]^+$ in which x=0, 1, 2, 3 or 4, and R is a branched or unbranched, saturated or unsaturated $C_{1-10}$-alkyl radical unsubstituted or mono- or polysubstituted, or a $C_{3-10}$-cycloalkyl radical, saturated or unsaturated, unsubstituted or mono- or polysubstituted, or two of the R radicals together with the nitrogen atom form a heterocyclyl, saturated or unsaturated, unsubstituted or mono- or polysubstituted, preferably a pyrrolidinyl, piperidinyl or morpholinyl. Very particular preference is given to (mono-) or (di-)lithium, (mono-) or (di-)sodium, (mono-) or (di-)potassium, magnesium or calcium salts.

Preferred embodiments of the compounds of the general formula (I) have the general formulae (Ia), (Ib) and (Ic)

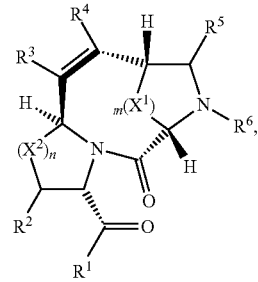

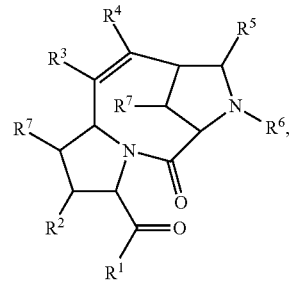

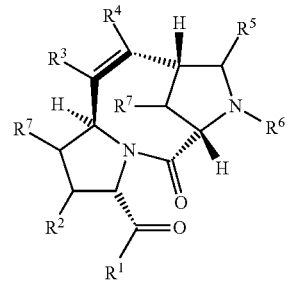

In a preferred embodiment of the inventive compounds of the general formula (I),
$X^1$ and $X^2$ are each $CH_2$;
m is 1 or 2, preferably 1;
n is 0, 1 or 2, preferably 1.

A person skilled in the art will recognize that the structure of the compounds of the general formulae (Ia), (Ib) and (Ic) derives from proline or diproline. The stereochemistry is preferably such that it derives from the L configuration of proline or diproline.

In a further preferred embodiment of the compounds of the general formula (I),
$R^1$ is $OR^8$; $NHR^8$ or $NHC(=O)R^8$; preferably $OR^8$,
  where $R^8$ is H; $C_{1-10}$-alkyl, saturated or unsaturated, branched or unbranched, unsubstituted or mono- or polysubstituted by one or more substituents each independently selected from the group consisting of F, Cl, Br, I, $C(=O)OH$, $C(=O)OC_{1-4}$-alkyl, $C(=O)C_{1-4}$-alkyl, $C(=O)NH$—$C_{1-4}$-alkyl, OH, O—$C_{1-4}$-alkyl, =O, $NH_2$, $NHC(=O)C_{1-4}$-alkyl, $NHS(=O)_2C_{1-4}$-alkyl, $S(=O)_2OH$, $S(=O)_2OC_{1-4}$-alkyl and $S(=O)_2$$C_{1-4}$-alkyl; aryl, unsubstituted or mono- or polysubstituted by one or more substituents each independently selected from the group consisting of F, Cl, Br, I, $C_{1-4}$-alkyl, $C(=O)OH$, $C(=O)OC_{1-4}$-alkyl, $C(=O)C_{1-4}$-alkyl, $C(=O)NH$—$C_{1-4}$-alkyl, OH, O—$C_{1-4}$-alkyl, $NH_2$, $NHC(=O)C_{1-4}$-alkyl, $NHS(=O)_2C_{1-4}$-alkyl, $S(=O)_2OH$, $S(=O)_2C_{1-4}$-alkyl and $S(=O)_2C_{1-4}$-alkyl; or $C_{1-8}$-alkyl-bridged aryl, unsubstituted or mono- or polysubstituted by one or more substituents each independently selected from the group consisting of F, Cl, Br, I, $C_{1-4}$-alkyl, C(=O)OH, C(=O)O$C_{1-4}$-alkyl, C(=O)$C_{1-4}$-alkyl, C(=O)NH—$C_{1-4}$-alkyl, OH, O—$C_{1-4}$-alkyl, $NH_2$, NHC(=O)$C_{1-4}$-alkyl, NHS(=O)$_2$$C_{1-4}$-alkyl, S(=O)$_2$OH, S(=O)$_2$O$C_{1-4}$-alkyl and S(=O)$_2$$C_{1-4}$-alkyl; where the alkyl chain may in each case be branched or unbranched, saturated or unsaturated, unsubstituted;

or $R^1$ is —NHCHR$^a$C(=O)—R$^b$ where $R^a$ is selected from the group consisting of —H, —$CH_3$, —CH($CH_3$)$_2$, —$CH_2$CH($CH_3$)$_2$, —CH($CH_3$)$CH_2CH_3$, —$CH_2CH_2SCH_3$, —$CH_2C_6H_5$, —$CH_2$-indolyl, —$CH_2$OH, —CH(OH)$CH_3$, —$CH_2$C(=O)$NH_2$, $CH_2CH_2$C(=O)$NH_2$, —$CH_2$—$C_6H_4$—OH, —$CH_2$SH, —$CH_2CH_2CH_2CH_2NH_2$, —$CH_2CH_2CH_2$NHC(=NH)$NH_2$, —$CH_2$-imidazolyl, —$CH_2CO_2H$, and —$CH_2CH_2CO_2H$; and $R^b$ is selected from —OH and -peptidyl, where the peptidyl is bonded covalently via its N terminus.

Preferably, $R^1$ is OH or $R^1$ is —NHCHR$^a$C(=O)—R$^b$ where $R^a$ is selected from the group consisting of —H, —$CH_3$, —CH($CH_3$)$_2$, —$CH_2$CH($CH_3$)$_2$, —CH($CH_3$)$CH_2CH_3$, —$CH_2CH_2SCH_3$, —$CH_2C_6H_5$, —$CH_2$-indolyl, —$CH_2$OH, —CH(OH)$CH_3$, —$CH_2$C(=O)$NH_2$, $CH_2CH_2$C(=O)$NH_2$, —$CH_2$—$C_6H_4$—OH, —$CH_2$SH, —$CH_2CH_2CH_2CH_2NH_2$, —$CH_2CH_2CH_2$NHC(=NH)$NH_2$, —$CH_2$-imidazolyl, —$CH_2CO_2H$, and —$CH_2CH_2CO_2H$; and $R^b$ is selected from —OH and -peptidyl, where the peptidyl is bonded covalently via its N terminus.

More preferably, $R^1$ is OH or —NHCH$_2$C(=O)-peptidyl.

In a particularly preferred embodiment, $R^1$ is OH.

In another particularly preferred embodiment, $R^1$ is —NHCH$_2$C(=O)-peptidyl.

In a further preferred embodiment of the compounds of the general formula (I)

$R^2$ and $R^5$ are each independently H; $C_{1-10}$-alkyl, saturated or unsaturated, branched or unbranched, unsubstituted, and $R^3$ and $R^4$ are each independently H; $C_{1-10}$-alkyl, saturated or unsaturated, branched or unbranched, unsubstituted.

Preferably, $R^2$, $R^3$, $R^4$ and $R^5$ are each H.

In a further preferred embodiment of the compounds of the general formula (I)

$R^6$ is H; $C_{1-10}$-alkyl, saturated or unsaturated, branched or unbranched, unsubstituted or mono- or polysubstituted by one or more substituents each independently selected from the group consisting of F, Cl, Br, I, C(=O)OH, C(=O)O$C_{1-4}$-alkyl, C(=O)$C_{1-4}$-alkyl, C(=O)NH—$C_{1-4}$-alkyl, OH, O—$C_{1-4}$-alkyl, =O, $NH_2$, NHC(=O)$C_{1-4}$-alkyl, NHS(=O)$_2$$C_{1-4}$-alkyl, S(=O)$_2$OH, S(=O)$_2$O$C_{1-4}$-alkyl and S(=O)$_2$$C_{1-4}$-alkyl;

or is C(=O)$R^{10}$; C(=O)O$R^{10}$; C(=O)N$R^{10}R^{11}$; S(=O)$_2$—$R^{10}$; S(=O)$_2$O$R^{10}$; or S(=O)$_2$N$R^{10}R^{11}$, where $R^{10}$ and $R^{11}$ are each independently H; $C_{1-10}$-alkyl, saturated or unsaturated, branched or unbranched, unsubstituted or mono- or polysubstituted by one or more substituents each independently selected from the group consisting of F, Cl, Br, I, $C_{1-4}$-alkyl, C(=O)OH, C(=O)O$C_{1-4}$-alkyl, C(=O)$C_{1-4}$-alkyl, C(=O)NH—$C_{1-4}$-alkyl, OH, O—$C_{1-4}$-alkyl, =O, $NH_2$, NHC(=O)$C_{1-4}$-alkyl, NHS(=O)$_2$$C_{1-4}$-alkyl, S(=O)$_2$OH, S(=O)$_2$O$C_{1-4}$-alkyl and S(=O)$_2$$C_{1-4}$-alkyl; aryl or heteroaryl, unsubstituted or mono- or polysubstituted by one or more substituents each independently selected from the group consisting of F, Cl, Br, I, $C_{1-4}$-alkyl, C(=O)OH, C(=O)O$C_{1-4}$-alkyl, C(=O)$C_{1-4}$-alkyl, C(=O)NH—$C_{1-4}$-alkyl, OH, O—$C_{1-4}$-alkyl, $NH_2$, NHC(=O)$C_{1-4}$-alkyl, NHS(=O)$_2$$C_{1-4}$-alkyl, S(=O)$_2$OH, S(=O)$_2$O$C_{1-4}$-alkyl and S(=O)$_2$$C_{1-4}$-alkyl; or $C_{1-8}$-alkyl-bridged aryl or heteroaryl, unsubstituted or mono- or polysubstituted by one or more substituents each independently selected from the group consisting of F, Cl, Br, I, $C_{1-4}$-alkyl, C(=O)OH, C(=O)O$C_{1-4}$-alkyl, C(=O)$C_{1-4}$-alkyl, C(=O)NH—$C_{1-4}$-alkyl, OH, O—$C_{1-4}$-alkyl, $NH_2$, NHC(=O)$C_{1-4}$-alkyl, NHS(=O)$_2$$C_{1-4}$-alkyl, S(=O)$_2$OH, S(=O)$_2$O$C_{1-4}$-alkyl and S(=O)$_2$$C_{1-4}$-alkyl; where the alkyl chain may in each case be branched or unbranched, saturated or unsaturated, unsubstituted;

or $R^6$ is —C(=O)—CHR$^y$NHR$^z$ where $R^y$ is selected from the group consisting of —H, —$CH_3$, —CH($CH_3$)$_2$, —$CH_2$CH($CH_3$)$_2$, —CH($CH_3$)$CH_2CH_3$, —$CH_2CH_2SCH_3$, —$CH_2C_6H_5$, —$CH_2$-indolyl, —$CH_2$OH, —CH(OH)$CH_3$, —$CH_2$C(=O)$NH_2$, $CH_2CH_2$C(=O)$NH_2$, —$CH_2$—$C_6H_4$—OH, —$CH_2$SH, —$CH_2CH_2CH_2CH_2NH_2$, —$CH_2CH_2CH_2$NHC(=NH)$NH_2$, —$CH_2$-imidazolyl, —$CH_2CO_2H$, and —$CH_2CH_2CO_2H$; and $R^z$ is selected from —H and —C(=O)—$C_{1-8}$-alkyl.

Preferably, $R^6$ is C(=O)$R^{10}$ or C(=O)O$R^{10}$, where $R^{10}$ is $C_{1-8}$-alkyl-bridged aryl, unsubstituted, more preferably $C_{1-8}$-alkyl-bridged fluorenyl, or $R^6$ is —C(=O)—CHR$^y$NHR$^z$ where $R^y$ is selected from the group consisting of —H, —$CH_3$, —CH($CH_3$)$_2$, —$CH_2$CH($CH_3$)$_2$, —CH($CH_3$)$CH_2CH_3$, —$CH_2CH_2SCH_3$, —$CH_2C_6H_5$, —$CH_2$-indolyl, —$CH_2$OH, —CH(OH)$CH_3$, —$CH_2$C(=O)$NH_2$, $CH_2CH_2$C(=O)$NH_2$, —$CH_2$—$C_6H_4$—OH, —$CH_2$SH, —$CH_2CH_2CH_2CH_2NH_2$, —$CH_2CH_2CH_2$NHC(=NH)$NH_2$, —$CH_2$-imidazolyl, —$CH_2CO_2H$, and —$CH_2CH_2CO_2H$; and $R^z$ is selected from —H and —C(=O)—$C_{1-8}$-alkyl.

More preferably, $R^6$ is an Fmoc group (fluorenylmethoxycarbonyl group) or $R^6$ is —C(=O)—CH$_2$NHC(=O)$CH_3$.

In a particularly preferred embodiment, $R^6$ is an Fmoc group.

In another particularly preferred embodiment, $R^6$ is —C(=O)—CH$_2$NH—C(=O)$CH_3$.

In a particularly preferred embodiment of the compounds of the general formula (I), $X^1$ and $X^2$ are each $CH_2$;

m and n are each 1;

$R^1$ is O$R^8$;

where $R^8$ is H; $C_{1-10}$-alkyl, saturated or unsaturated, branched or unbranched, unsubstituted or mono- or polysubstituted by one or more substituents each independently selected from the group consisting of C(=O)OH, C(=O)O$C_{1-4}$-alkyl, C(=O)$C_{1-4}$-alkyl, C(=O)NH—$C_{1-4}$-alkyl, OH, O—$C_{1-4}$-alkyl, =O, $NH_2$, NHC(=O)$C_{1-4}$-alkyl, NHS(=O)$_2$$C_{1-4}$-alkyl, S(=O)$_2$OH, S(=O)$_2$O$C_{1-4}$-alkyl and S(=O)$_2$$C_{1-4}$-alkyl; or $C_{1-8}$-alkyl-bridged aryl, unsubstituted or mono- or polysubstituted by one or more substituents each independently selected from the group consisting of F, Cl, Br, I, $C_{1-4}$-alkyl, C(=O)OH, C(=O)O$C_{1-4}$-alkyl, C(=O)$C_{1-4}$-alkyl, C(=O)NH—$C_{1-4}$-alkyl, OH, O—$C_{1-4}$-alkyl, $NH_2$, NHC(=O)$C_{1-4}$-alkyl, NHS(=O)$_2$$C_{1-4}$-alkyl, S(=O)$_2$OH, S(=O)$_2$O$C_{1-4}$-alkyl and S(=O)$_2$$C_{1-4}$-alkyl; where the alkyl chain may in each case be branched or unbranched, saturated or unsaturated, unsubstituted;

or $R^1$ is —NHCHR$^a$C(=O)—R$^b$ where $R^a$ is selected from the group consisting of —H, —CH$_3$, —CH(CH$_3$)$_2$, —CH$_2$CH(CH$_3$)$_2$, —CH(CH$_3$)CH$_2$CH$_3$, —CH$_2$CH$_2$SCH$_3$, —CH$_2$C$_6$H$_5$, —CH$_2$-indolyl, —CH$_2$OH, —CH(OH)CH$_3$, —CH$_2$C(=O)NH$_2$, CH$_2$CH$_2$C(=O)NH$_2$, —CH$_2$—C$_6$H$_4$—OH, —CH$_2$SH, —CH$_2$CH$_2$CH$_2$CH$_2$NH$_2$, —CH$_2$CH$_2$CH$_2$NHC(=NH)NH$_2$, —CH$_2$-imidazolyl, —CH$_2$CO$_2$H, and —CH$_2$CH$_2$CO$_2$H; and $R^b$ is selected from —OH and -peptidyl, where the peptidyl is bonded covalently via its N terminus;

$R^2$ and $R^5$ are each H;

$R^3$ and $R^4$ are each H;

$R^6$ is H; $C_{1-10}$-alkyl, saturated or unsaturated, branched or unbranched, unsubstituted or mono- or polysubstituted by one or more substituents each independently selected from the group consisting of C(=O)OH, C(=O)OC$_{1-4}$-alkyl, C(=O)C$_{1-4}$-alkyl, C(=O)NH—C$_{1-4}$-alkyl, OH, O—C$_{1-4}$-alkyl, =O, NH$_2$, NHC(=O)C$_{1-4}$-alkyl and NHC(=O)$_2$C$_{1-4}$-alkyl; or is C(=O)R$^{10}$; C(=O)OR$^{10}$; C(=O)NR$^{10}$R$^{11}$; S(=O)$_2$—R$^{10}$; S(=O)$_2$OR$^{10}$; or S(=O)$_2$NR$^{10}$R$^{11}$, where $R^{10}$ and $R^{11}$ are each independently H; $C_{1-10}$-alkyl, saturated or unsaturated, branched or unbranched, unsubstituted or mono- or polysubstituted by one or more substituents each independently selected from the group consisting of $C_{1-4}$-alkyl, C(=O)OH, C(=O)OC$_{1-4}$-alkyl, C(=O)C$_{1-4}$-alkyl, C(=O)NH—C$_{1-4}$-alkyl, OH, O—C$_{1-4}$-alkyl, =O, NH$_2$, NHC(=O)C$_{1-4}$-alkyl, NHS(=O)$_2$C$_{1-4}$-alkyl; aryl, unsubstituted or mono- or polysubstituted by one or more substituents each independently selected from the group consisting of $C_{1-4}$-alkyl, C(=O)OH, C(=O)OC$_{1-4}$-alkyl, C(=O)C$_{1-4}$-alkyl, C(=O)NH—C$_{1-4}$-alkyl, OH, O—C$_{1-4}$-alkyl, NH$_2$, NHC(=O)C$_{1-4}$-alkyl, NHS(=O)$_2$C$_{1-4}$-alkyl; or $C_{1-8}$-alkyl-bridged aryl or heteroaryl, in each case unsubstituted or mono- or polysubstituted by one or more substituents each independently selected from the group consisting of F, Cl, Br, I, $C_{1-4}$-alkyl, C(=O)OH, C(=O)OC$_{1-4}$-alkyl, C(=O)C$_{1-4}$-alkyl, C(=O)NH—C$_{1-4}$-alkyl, OH, O—C$_{1-4}$-alkyl, NH$_2$, NHC(=O)C$_{1-4}$-alkyl, NHS(=O)$_2$C$_{1-4}$-alkyl, where the alkyl chain may in each case be branched or unbranched, saturated or unsaturated, unsubstituted;

or $R^6$ is —C(=O)—CHR$^y$NHR$^z$ where $R^y$ is selected from the group consisting of —H, —CH$_3$, —CH(CH$_3$)$_2$, —CH$_2$CH(CH$_3$)z, —CH(CH$_3$)CH$_2$CH$_3$, —CH$_2$CH$_2$SCH$_3$, —CH$_2$C$_6$H$_5$, —CH$_2$-indolyl, —CH$_2$OH, —CH(OH)CH$_3$, —CH$_2$C(=O)NH$_2$, CH$_2$CH$_2$C(=O)NH$_2$, —CH$_2$—C$_6$H$_4$—OH, —CH$_2$SH, —CH$_2$CH$_2$CH$_2$CH$_2$NH$_2$, —CH$_2$CH$_2$CH$_2$NHC(=NH)NH$_2$, —CH$_2$-imidazolyl, —CH$_2$CO$_2$H, and —CH$_2$CH$_2$CO$_2$H; and $R^z$ is selected from —H and —C(=O)—C$_{1-8}$-alkyl.

The present invention further provides for the use of at least one compound of the general formula (I) for the induction of an α-helix conformation in at least one protein and/or peptide.

The present invention further provides a medicament comprising at least one inventive compound of the above-specified general formula (I) which preferably induces an α-helix conformation in at least one protein and/or peptide, in each case optionally in the form of one of the pure stereoisomers thereof, especially enantiomers or diastereomers, racemates thereof, or in the form of a mixture of stereoisomers, especially of enantiomers and/or diastereomers, in any mixing ratio, or in each case in the form of a corresponding salt, or in each case in the form of a corresponding solvate, and optionally one or more pharmaceutically acceptable excipients and/or optionally further active ingredients.

Preferred pharmaceutically acceptable excipients are, for example, fillers, extenders, binders, humectants, dissolution retardants, disintegrants, absorption accelerators, wetting agents, absorbents and/or lubricants.

In a preferred embodiment, the inventive medicament comprises at least one peptide and/or protein which has an α-helix conformation which has been induced by at least one inventive substituted compound of the general formula (I) present in the inventive medicament.

The inventive medicament may be present as a liquid, semisolid or solid dosage form, for example in the form of injection solutions, droplets, juices, syrups, sprays, suspensions, tablets, patches, capsules, plasters, suppositories, ointments, creams, lotions, gels, emulsions, aerosols, or in multiparticulate form, for example in the form of pellets or granules, optionally pressed to tablets, dispensed in capsules or suspended in a liquid, and may also be administered as such.

These inventive medicaments are especially suitable for induction of the formation of an α-helix conformation in peptides and/or proteins and are therefore especially suitable in medicaments for prophylaxis and/or treatment of disorders or diseases at least partly associated with the induction of an α-helix conformation in at least one protein and/or at least one peptide.

The present invention therefore further provides for the use of at least one substituted compound of the general formula (I) for production of a medicament for treatment and/or prophylaxis of one or more diseases and/or disorders associated at least partly with the induction of an α-helix conformation in at least one protein and/or at least one peptide.

The inventive medicament is preferentially suitable for treatment and/or prophylaxis of one or more diseases and/or disorders selected from the group consisting of bacterial and viral infection diseases, neurodegenerative disorders and tumor disorders.

Further diseases in the context of the invention which can be treated with the inventive medicaments are selected from the group comprising monkey pox, AIDS, anthrax (*Bacillus anthracia*), avian influenza (avian plague, bird flu), borreliosis, *Borrelia recurrentis* (relapsing louse fever), botulism (*Clostridium botulinum*), brucellosis, *campylobacter* infections, chlamydiosis, cholera (*Vibrio cholera*), Creutzfeld-Wakob disease, *Coxiella burnetii* (Q fever), *Cryptosporidium parvuum* (cryptosporidiosis), dengue fever, diphtheria, ebola virus infections, echinococcosis (fox tapeworm, dog tapeworm), EHEC infections (STEC infections, VTEC infections), enteroviruses, typhus (*Rickettsia prowazeckii*), *Francisella tularensis* (tularemia), early summer meningoencephalitis (ESME), yellow fever, giardiasis, gonorrhea, flu (influenza), *Haemophilis influenza*, hantavirus, *Helicobacter pylori*, hepatitis A, hepatitis B, hepatitis C, hepatitis D, hepatitis E, herpes, HUS (hemolytic uremic syndrome), epidemic keratoconjunctivitis, whooping cough (pertussis), infantile paralysis (poliomyelitis), head lice infestation, scabies, Crimean-Congo fever, Lassa fever, food-related disorders, legionellosis, leishmaniasis, leprosy, leptospirosis, listeriosis, Lyme borreliasis, Lymphogranuloma venereum, malaria, (plasmodia infections), Marburg virus infections, measles, meliodiosis, meningococcal diseases, MRSA (Staphylococci), mumps, mycoses (fungal infections), newly and increasingly occurring infection disorders, noroviruses, ornithosis (parrot disease), papillomaviruses, paratyphus, plague (*Yersinia pestis*), pneumococcal infections (*Streptococcus pneumonia*), smallpox, travel-associated infection disorders, tapeworm infection in humans, rotaviruses, rubella, RSV infections, salmonellosis, scarlet fever, severe acute respiratory syndrome (SARS), sexually transmitted infections, shigellosis, syphilis, tetanus, rabies, toxoplasmosis, trichinellosis, tuberculosis, typhus, varicella (chickenpox), variant Creutzfeldt-Jakob disease, viral hemorrhagic fever, West Nile fever, yersiniosis and/or tick-transmitted diseases.

The bacterial diseases are preferably diseases associated, especially mediated, by the following bacteria: *legionella*, streptococci, staphylococci, *klebsiella*, *Haemophilis influenza*, *rickettsia* (typhus), mycobacteria, mycoplasmas, ureaplasmas, *neisseria* (meningitis, Waterhouse-Friedrichsen syndrome, gonorrhea), pseudomonads, *bordetella* (pertussis), corynobacteria (diphtheria), *Chlamydia*, *campylobacter* (diarrhea), *Escherichia coli*, *proteus*, *salmonella*, *shigella*, *Yesinia*, *vibrios*, *enterococcii*, *clostridia*, *borrelia*, *Treponema pallidum*, *brucelli*, *francisella* and/or *leptospira*, especially *listeria*.

Particularly preferred diseases are those which are triggered by *listeria* selected from the group comprising *L. monocytogenes* Sv1/2a, *L. monocytogenes* Sv4b F2365, *L. monocytogenes* Sv4b H7858, 178 contigs, *L. monocytogenes* Sv1/2a F6854, 133 contigs, *L. monocytogenes* Sv4b, *L. monocytogenes* Sv4a, *L. innocua* Sv6a, *L. welshimeri* Sv6b, *L. seeligeri* Sv1/2b and/or *L. ivanovii* Sv5, or essentially originate from the preferred *listeria* specified.

The preferred neurodegenerative diseases are selected from the group comprising Alzheimer's disease, Parkinson's disease, Huntington's disease and/or amyotrophic lateral sclerosis (ALS). Neurodegenerative disorders in the context of the invention are also Alexander's disease, Alpers-Huttenlocher syndrome, Huntingdon's disease, Creutzfeldt-Jakob disease, extrapyramidal syndrome, Friedreich's ataxia, corticobasal degeneration, Crabbe disease, leukodystrophy, Lewy body dementia, mask-like face, Pick's disease, multiple sclerosis, multisystem atrophy, neurodegenerative iron deposits in the brain, progressive supranuclear palsy, Shy-Drager syndrome, spinocerebellar ataxia, synucleinopathy and/or tropic spastic paraparesis.

The preferred tumor disorders are selected from the group comprising tumor disorders of the ear/nose/throat region, of the lung, of the mediastinum, of the gastrointestinal tract, of the urogenital system, of the gynecological system, of the breast, of the endocrine system, of the skin, bone and soft tissue sarcomas, mesotheliomas, melanomas, neoplasms of the central nervous system, cancers or tumor disorders in childhood, lymphomas, leukemias, paraneoplastic syndromes, metastases without known primary tumor (CUP syndrome), peritoneal carcinomatoses, immunosuppression-related malignancies and/or tumor metastases.

More particularly, the tumors may be of the following types of cancer: adenocarcinoma of the breast, of the prostate and of the colon; all types of lung cancer derived from the bronchia; bone marrow cancer, melanoma, hepatoma, neuroblastoma; papilloma; apudoma, choristoma, branchioma; malignant carcinoid syndrome; carcinoid heart disease; carcinoma (for example Walker's carcinoma, basal cell carcinoma, basosquamous carcinoma, Brown-Pearce carcinoma, ductal carcinoma, Ehrlich's tumor, carcinoma in situ, Krebs-2 carcinoma, Merkel cell carcinoma, mucous carcinoma, non-small-cell bronchial carcinoma, oat cell carcinoma, papillary carcinoma, scirrhous carcinoma, bronchiole-alveolar carcinoma (bronchial carcinoma, squamous cell carcinoma and transitional cell carcinoma); histiocytic dysfunction; leukemia (for example in connection with B-cell leukemia, mixed cell leukemia, null cell leukemia, T-cell leukemia, chronic T-cell leukemia, HTLV II-associated leukemia, acute lymphocytic leukemia, chronic lymphocytic leukemia, mast cell leukemia and myeloid leukemia); malignant histiocytosis, Hodgkin's disease, non-Hodgkin lymphoma, solitary plasma cell tumor; reticuloendotheliosis, chondroblastoma; chondroma, chondrosarcoma; fibroma; fibrosarcoma; giant cell tumors; histiocytoma; lipoma; liposarcoma; leukosarcoma; mesothelioma, myxoma, myxosarcoma; osteoma; osteosarcoma; Ewing's sarcoma; synovioma; adenofibroma; adenolymphoma; carcinosarcoma, chordoma, craniopharyngioma, dysgerminoma, hamartoma; mesenchymoma; mesonephroma, myosarcoma, ameloblastoma, cementoma; odontoma; teratoma; thymoma, chorioblastoma; adenocarcinoma, adenoma; cholangioma; cholesteatoma; cylindroma; cystadenocarcinoma, cystadenoma; granulose cell tumor; gynadroblastoma; hidradenoma; islet cell tumor; Leydig cell tumor; papilloma, sertoli cell tumor, theca cell tumor, leiomyoma; leiomyosarcoma; myoblastoma; myoma; myosarcoma; rhabdomyoma; rhabdomyosarcoma; ependynoma; ganglioneuroma, glioma; medulloblastoma, meningioma; neurilemmoma; neuroblastoma; neuroepithelioma, neurofibroma, neuroma, paraganglioma, non-chromaffin paraganglioma, angiokeratoma, angiolymphoid hyperplasia with eosinophilia; sclerosing angiomas; angiomatosis; glomangioma; hemangioendothelioma; hemangioma; hemangiopericytoma, hemangiosarcoma; lymphangioma, lymphangiomyoma, lymphangiosarcoma; pinealoma; cystosarcoma phyllodes; hemangiosarcoma; lymphangiosarcoma; myxosarcoma, ovarian carcinoma; sarcoma (for example Ewing's sarcoma, experimentally, caposi sarcoma and mast cell sarcoma); neoplasms (for example bone neoplasms, breast neoplasms, neoplasms of the digestive system, colorectal neoplasms, liver neoplasms, pancreatic neoplasms, pituitary neoplasms, testicular neoplasms, orbital neoplasms, neoplasms of the head and neck, of the central nervous system, neoplasms of the hearing organ, of the pelvis, of the respiratory tract and of the urogenital tract); neurofibromatosis and cervical squamous cell dysplasia. In a further preferred embodiment, the cancer or the tumor is selected from the group: tumors of the ear/nose/throat region including tumors of the inner nose, of the paranasal sinuses, of the nasopharynx, of the lips, of the oral cavity, of the oropharynx, of the larynx, of the hypopharynx, of the ear, of the salivary glands and paragangliomas, tumors of the lung including non-small-cell bronchial carcinomas, small cell bronchial carcinomas, tumors of the mediastinum, tumors of the gastrointestinal tract including tumors of the esophagus, of the stomach, of the pancreas, of the liver, of the gall bladder and of the biliary tract, of the small bowel, colon and rectal carcinomas and anal carcinomas, urogenital tumors including tumors of the kidneys, of the ureter, of the bladder, of the prostate, of the urethra, of the penis and of the testis, gynecological tumors including tumors of the cervix, of the vagina, of the vulva, corpus carcinoma, malignant trophoblastic disease, ovarian carcinoma, tumors of the uterine tube (tuba faloppii), tumors of the abdominal cavity, carcinomas of the breast, tumors of endocrine organs including tumors of the thyroid, of the parathyroid, of the adrenal cortex, endocrine pancreatic tumors, carcinoid tumors and carcinoid syndrome, multiple endocrine neoplasms, bone and soft tissue sarcomas, mesotheliomas, skin tumors, melanomas including cutaneous and intraocular melanomas, tumors of the central nervous system, tumors in childhood including retinoblastoma, Wilm's tumor, neurofibromatosis, neuroblastoma, Ewing's sarcoma tumor family, rhabdomyosarcoma, lymphomas including non-Hodgkin lymphomas, cutaneous T-cell lymphomas, primary lymphomas of the central nervous system, Hodgkin's disease, leukemias including acute leukemias, chronic myeloid and lymphatic leukemias, plasma cell neoplasms, myelodysplastic syndromes, paraneoplastic syndromes, metastases without known primary tumor (CUP syndrome), peritoneal carcinomatosis, immunosuppression-related malignancy including AIDS-related malignancies such as Kaposi's sarcoma, AIDS-associated lymphomas, AIDS-associated lymphomas of the central nervous system, AIDS-associated Hodgkin's disease and AIDS-associated anogenital tumors, transplantation-related malignancies, metastatic tumors including brain metastases, lung metastases, liver metastases, bone metastases, pleural and pericardial metastases and malignant ascites.

In a further preferred embodiment, the cancer or the tumor is selected from the group comprising cancers or tumor disorders of the carcinomas of the breast, of the gastrointestinal tumors, including colon carcinomas, gastric carcinomas, pancreatic carcinomas, colon cancer, small bowel cancer, of the ovarian carcinomas, of the cervical carcinomas, lung cancer, prostate cancer, renal cell carcinomas and/or liver metastases.

Viral diseases in the context of the invention are selected from the group comprising influenza, cold, cough, measles, mumps, rubella, fifth disease, three-day fever, chickenpox, Preiffer's glandular fever, SARS, zytomegalo virus, diarrhea, hepatitis, polio, labial herpes, warts, rabies, assa fever, ebola, Marburg fever, hantavirus fever, ESME, RSSE, Louping-ill encephalitis, Powassan encephalitis, Kyasanur forest fever, Omsk hemorrhagic fever, Colorado tick fever, yellow fever, Dengue fever, Japanese encephalitis, West Nile fever, Chikungunya fever, O'nyong-nyong fever, Rift Valley fever, sandfly fever, Ross River fever, Sindbis fever, Mayaro fever, Murray valley encephalitis, St. Louis encephalitis, Rocio encephalitis, California encephalitis, Bunyamwera fever, Oropouche fever, AIDS, genital herpes and/or Herpes Simplex; more preferably, the viral hepatitis diseases are selected from the group comprising hepatitis A, hepatitis B, hepatitis C, hepatitis D, hepatitis E, hepatitis F, hepatitis G and/or autoimmune hepatitis and/or asymptomatic or symptomatic HIV infections.

HIV infections can lead to AIDS. In the context of the invention, AIDS is characterized or classified by a clinical picture selected from the group comprising
(a) asymptomatic or symptomatic HIV infections, (b) bacillary angiomatoses, inflammations of the pelvis minor, particularly in the case of complications in a tube abscess or ovarian abscess, extended or recurrent Herpes zoster, thrombocytopenic purpura, long-lasting fever or diarrhea lasting for longer than one month, listeriosis, oral hairy leukoplakia, oropharyngeal candidiasis, chronic or difficult-to-treat vaginal candidiasis, cervical displasias, carcinoma in situ, peripheral neuropathy and/or (c) candidiasis of the respiratory pathways or of the food tubes, cytomegalievirus infections, CMV retinitis, HIV-related encephalopathy, herpes simplex with chronic ulcers (>1 month) or herpes simplex-related bronchitis, pneumonia or oesophagitis, chronic histoplasmosis, intestinal isosporiasis, Kaposi's sarkoma, disseminated or extrapulmonary coccidiomycosis, extrapulmonary cryptokoccosis, chronic intestinal kryptosporidiosis, immunoblastic, primary cerebral or Burkitt's lymphoma, extrapulmonary mycobacteria, *pneumocystis* pneumonia, recurrent bacterial pneumonia, progressive multifocal leucoencephalopathy, recurrent *Salmonella* septicemia, tuberculosis, cerebral toxoplasmosis, wasting syndrome and/or invasive cervical carcinoma. Treatment in the context of the invention means prophylaxis, therapy, monitoring of the course and/or after-treatment of diseases.

In the treatment of the diseases mentioned, it is particularly preferable to formulate and/or administer the inventive medicament as a gel, powder, tablet, sustained release tablet, premix, emulsion, cast formulation, droplet, concentrate, granular material, syrup, pellet, bolus, capsule, aerosol, spray and/or inhalate.

The inventive medicament is preferably present in a concentration of 0.1 to 99.5%, preferably of 0.5 to 95.0%, and more preferably of 20.0 to 80.0% by weight in a formulation.

This formulation is preferably placed orally, subcutaneously, intravenously, intramuscularly, intraperitoneally and/or topically.

The inventive medicament is preferably used in total amounts of 0.05 to 500 mg per kg, preferably of 5 to 100 mg per kg of body weight, every 24 hours.

The contacting is preferably effected orally, via injection, topically, vaginally, rectally and/or nasally.

The present invention further provides for the use of at least one substituted compound of the general formula (I) for production of a substance library of α-helix-induced proteins and/or peptides.

A substance library of proteins and/or peptides having an α-helix conformation which has been induced by at least one substituted compound of the general formula (I) likewise forms part of the subject matter of the present invention.

The present invention further provides a process for producing a peptide library, comprising the step of:
Incorporating an inventive compound of the general formula (I) into a peptide sequence.

Preference is given to a process in which an inventive compound of the general formula (I) is flanked immediately by a glycine residue on each side within the sequence.

Preference is likewise given to a process in which the N-terminus of the sequence is acylated.

The processes customary for production of peptide libraries and the processes customary for incorporation of individual compounds into peptide sequences are known to those skilled in the art. A preferred process for production of peptide libraries is solid phase synthesis. For this purpose, preference is given to a sequential buildup of the peptides using suitably protected units, which are commercially available. In order to ensure compatibility of the inventive compounds with the particular chemistry of the solid phase synthesis selected, the inventive compounds for this purpose are preferably protected with compatible protecting groups. If the solid phase synthesis is based, for example, on Fmoc-protected amino acid units, the inventive compounds are preferably also Fmoc-protected.

A particularly preferred inventive compound therefore has the following structure:

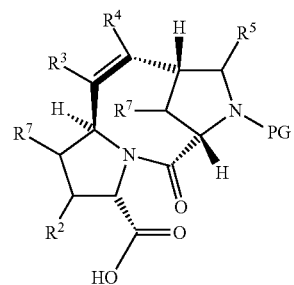

where, preferably, $R^2$ to $R^5$ and $R^7$ are each —H and PG is a suitable protecting group, preferably Fmoc.

The present invention further provides a peptide library obtainable by the above processes.

The invention further provides processes for preparing the inventive substituted compounds of the general formula (I).

The chemicals and reaction components used in the reactions described hereinafter are commercially available or can each be prepared by customary methods known to those skilled in the art.

General Preparation Process

Scheme 1:

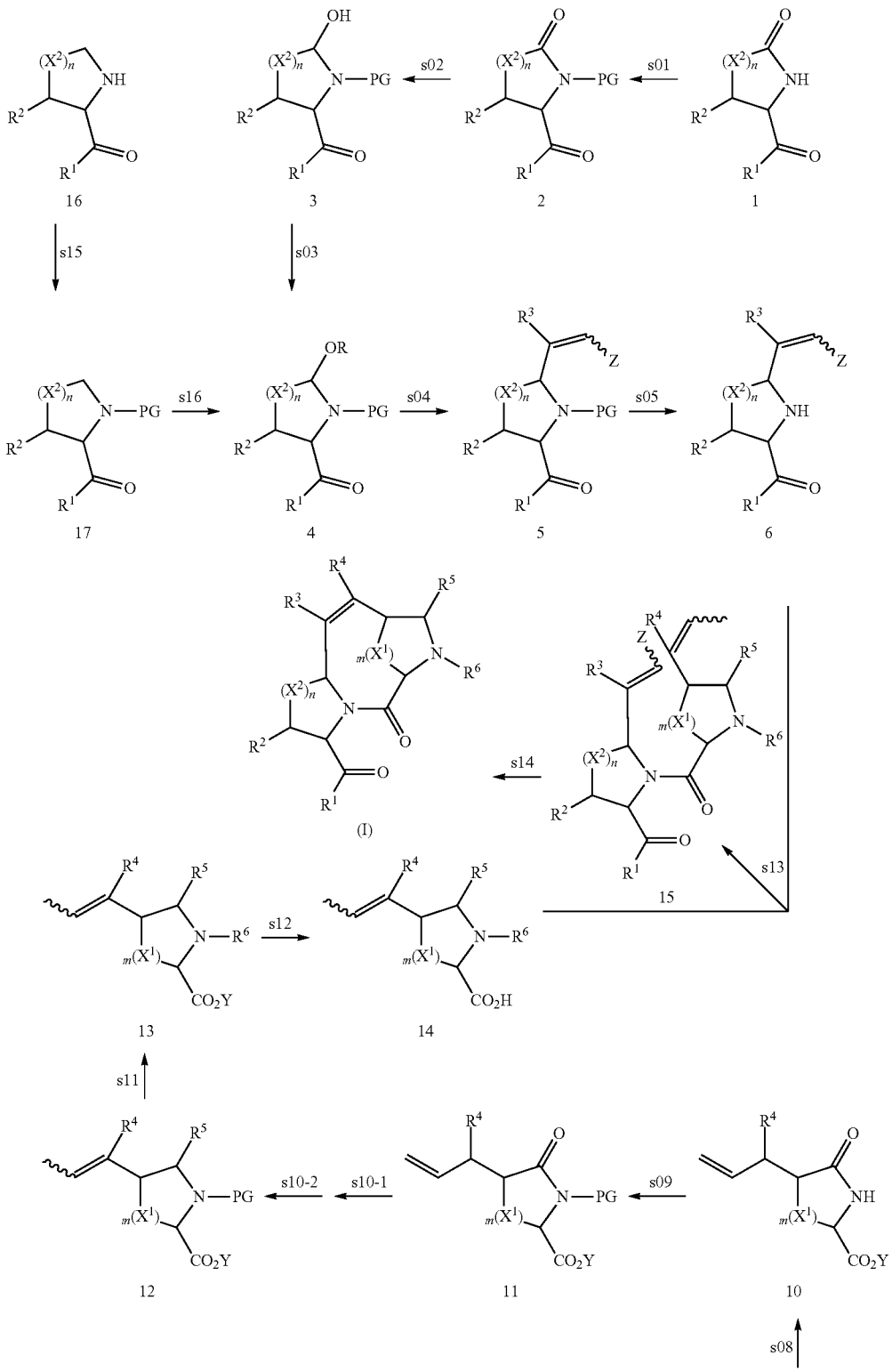

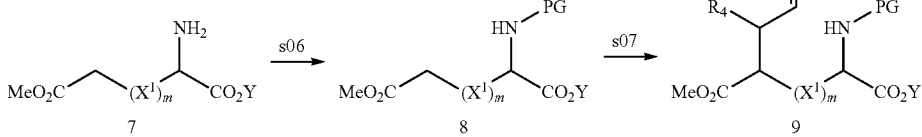

In steps s01 and s15, the secondary amino function of the compounds of the general formula 1 or 16 is protected by means of methods familiar to those skilled in the art, by introduction of a protecting group (PG) for example a Boc or an Moc protecting group, optionally in the presence of a base such as triethylamine or 4-dimethylaminopyridine.

In step s02, the keto group of the compounds of the general formula 2 is reduced to give alcohols of the general formula 3 by means of methods familiar to those skilled in the art in a reaction medium, preferably selected from the group consisting of diethyl ether, ethanol, acetic acid, methanol and tetrahydrofuran in the presence of a suitable reducing agent, preferably a metal hydride, more preferably selected from the group consisting of diisobutylaluminum hydride (DIBAL), sodium borohydride, sodium cyanoborohydride, lithium aluminum hydride or hydrogen, optionally with addition of a catalyst, preferably selected from the group consisting of palladium, platinum, platinum oxide or Raney nickel, optionally with addition of an organic base selected from the group consisting of ammonia, triethylamine and diisopropylethylamine.

In step s03, the OH function of the compounds of the general formula 3 is alkylated by means of methods familiar to those skilled in the art (i.e. substituted for an alkoxy group R), for example by reaction with an alcohol ROH in the presence of an acid, for example pyridine p-toluene sulfonate, and thus converted to a compound of the general formula 4. Preferred alcohols ROH are, for example, methanol, ethanol or other lower alkanols.

Alternatively, compounds of the general formula 4 can also be prepared by means of methods familiar to those skilled in the art, by means of a two-stage synthesis proceeding from compounds of the general formula 16 in which the amino function is first protected analogously to s01 in a step s15. Thereafter, the compounds of the general formula 17 are reacted electrochemically in a step s16, optionally in the presence of a base, with an alcohol ROH to give compounds of the general formula 4.

In step s04, compounds of the general formula 4 are converted by means of methods familiar to those skilled in the art to compounds of the general formula 5. For example, a Grignard reagent $Mg(CR^3=CH-Z)Hal$ (where Z=H or alkyl and Hal=chlorine, bromine or iodine, preferably bromine) is used, in the presence of a transition metal ion, preferably of a copper (I) compound, optionally in the presence of a base.

In step s05, the protecting group introduced beforehand for the secondary amino function of the compounds of the general formula 5 is detached by means of methods familiar to those skilled in the art, such as in the presence of trialkylsilyl halides or optionally in the presence of an acid, and compounds of the general formula 6 are thus obtained.

In step s06, the primary amino function of the compounds of the general formula 7 where Y=alkyl is protected with a suitable amine protecting group by means of methods familiar to those skilled in the art, analogously to steps s01 and s15.

In step s07, the compounds of the general formula 8 are first deprotonated selectively on the carbon atom in the α-position to the COOMe group by means of methods familiar to those skilled in the art, in the presence of a suitable base, for example lithium hexamethyldisilazide, and then allylated with an allyl halide $Hal-CHR^4-CH=CH_2$, preferably an allyl bromide, to give a compound of the general formula 9.

In step s08, the compounds of the general formula 9 are converted to compounds of the general formula 10 with ring closure by means of methods familiar to those skilled in the art, in the presence of an acid, for example aqueous phosphoric acid, with detachment of the amine protecting group.

In step s09, the secondary amino function of the cyclic compounds of the general formula 10 is protected with a suitable amine protecting group by means of methods familiar to those skilled in the art, analogously to steps s01, s06 and s15. A particularly preferred amine protecting group is a Boc group.

In step s10-1, the keto group of the compounds of the general formula 11 is reduced to the corresponding alcohol by means of methods familiar to those skilled in the art, in the presence of a suitable reducing agent, preferably a metal hydride, more preferably selected from the group consisting of diisobutyl aluminum hydride (DIBAL), sodium borohydride, sodium cyanoborohydride, lithium aluminum hydride and lithium triethylborohydride, and this alcohol is then hydrogenated in the presence of a suitable reducing agent to give the corresponding alkyl compounds ($R^5$=H). Alternatively, the alcohol function formed after the reduction of the keto group can also be converted to a better leaving group, for example by protonation or by a conversion by methods known to those skilled in the art to a better leaving group, for example a triflate group, and then substituted by $R^5$ ($R^5 \neq H$) in a substitution reaction, for example by a metal-catalyzed coupling reaction with $R^5-Hal$ where Hal=Cl, Br, I, preferably I.

In step s10-2, the double bond in the allyl side chain is isomerized, for which preference is given to employing metal-based catalysts known to those skilled in the art, especially based on Ru, Rh and Pd.

In step s11, the amine protecting group of 12 is detached analogously to s05, and the resulting free amino function is substituted in the N position by means of methods known to those skilled in the art, for example using a halide $R^6-Hal$, optionally in the presence of a base, where Hal is preferably Cl, Br or I, or by using a boronic acid $B(OH)_2R^6$ or a corresponding boronic ester, optionally in the presence of a coupling reagent and/or of a base, and the compound 13 is thus obtained. Alternatively, the protecting group PG, however, can also not be detached when it is itself a desired $R^6$ radical.

In step s12, the esters of the general formula 13 with the $CO_2Y$ group are cleaved to acids of the general formula 14 by means of methods familiar to those skilled in the art in a reaction medium, preferably selected from the group consisting of ethanol, methanol, MeCN, THF and water or any mixtures thereof, optionally with addition of an inorganic base, preferably potassium hydroxide, sodium hydroxide or lithium hydroxide, at temperatures of 0° C. to 120° C.

In step s13, the amine 6 is converted to the amide 15. This can be achieved, for example, first of all by conversion of the acid 14 to an acid halide, preferably an acid chloride, by means of methods familiar to those skilled in the art, for example by heating 14 in the presence of a suitable chlorinating agent, for example selected from the group of $(COCl)_2$, $PCl_3$, $POCl_3$ or $SOCl_2$ in a reaction medium, preferably selected from the group consisting of toluene, DMF, DCM and pyridine, at temperatures of −70° C. to 100° C., optionally in the presence of microwave radiation, and subsequent reaction of the acid chloride with 6, in a reaction medium, preferably selected from the group consisting of ether, THF, MeCN, MeOH, EtOH, DMF and DCM, with or without addition of at least one organic or inorganic base, for example $NEt_3$, DMAP, pyridine or DIPEA, optionally in the presence of at least one organic base, preferably selected from the group consisting of $NEt_3$, DMAP, pyridine and DIPEA, or of an inorganic base, at temperatures of preferably −70° C. to 100° C., optionally in the presence of microwave radiation, or achieved by reaction of 6 with the acid 14, in a reaction medium, preferably selected from the group consisting of diethyl ether, tetrahydrofuran, acetonitrile, methanol, ethanol, dimethylformamide and dichloromethane, optionally in the presence of at least one coupling reagent, preferably selected from the group consisting of 1-benzotriazolyloxytris (dimethylamino)phosphonium hexafluorophosphate (BOP), dicyclohexylcarbodiimide (DCC), diisopropylcarbodiimide (DIC), N'—(3-dimethyl-aminopropyl)-N-ethylcarbodiimide (EDCl), N—[(dimethylamino)-1H-1,2,3-triazolo[4,5-b]pyridino-1-ylmethylene]-N-methylmethanaminium hexafluorophosphate N-oxide (HATU), 0-(benzotriazol-1-yl)-N,N,N',N'-tetramethyluronium hexafluorophosphate (HBTU) and 1-hydroxy-7-azabenzotriazole (HOAt), optionally in the presence of at least one inorganic base, preferably selected from the group consisting of potassium carbonate and cesium carbonate, or of an organic base, preferably selected from the group consisting of triethylamine, pyridine, dimethylaminopyridine and diisopropylethylamine, preferably at temperatures of −70° C. to 150° C.

In step s14, the compound of the general formula 15 is converted to the compound of the general formula (I) in the course of a ring-closing metathesis by means of methods known to those skilled in the art, for example using Grubbs or Schrock catalysts, preferably Grubbs-I or Grubbs-II catalysts.

Alternatively to step s14, the compound of the general formula 15 is converted in step s17 to the dialdehyde 16 and then subjected in step s18 to an intramolecular McMurry coupling (see scheme 2). The dialdehyde is preferably synthesized by ozonolysis and subsequently reductive workup with, for example, Zn/acetic acid, $Pt/H_2$, triphenylphosphine or dimethyl sulfide. The McMurry coupling is performed by means of methods known to those skilled in the art. Preference is given to performing the McMurry coupling with low-valency titanium which is prepared in situ by reduction of titanium (III) chloride or titanium (IV) chloride with, for example, lithium aluminum hydride, zinc, Mg or copper/zinc.

Two-Stage Alternative to Step S14 of the General Preparation Process

Scheme 2:

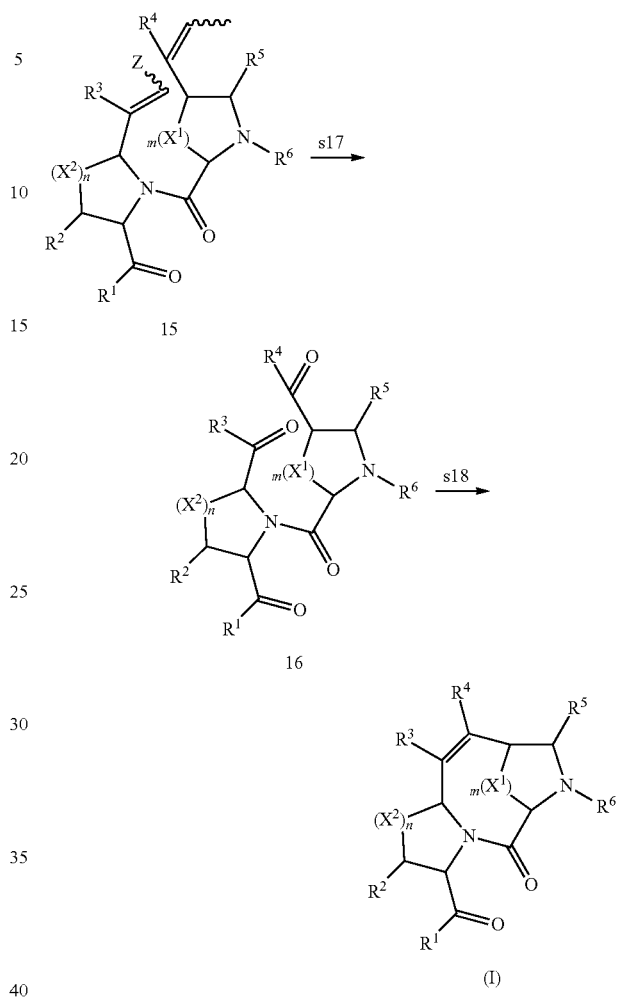

The methods familiar to those skilled in the art for performance of reaction steps s01 to s18 can be found in the standard works of organic chemistry, for example J. March, Advanced Organic Chemistry, Wiley & Sons, 6th edition, 2007; F. A. Carey, R. J. Sundberg, Advanced Organic Chemistry, Parts A and B, Springer, 5th edition, 2007); collective of authors, Compendium of Organic Synthetic Methods, Wiley & Sons. In addition, further methods and literature references can be dispensed by the standard databases, for example the Reaxys® database of Elsevier, Amsterdam, the Netherlands, or the SciFinder® database of the American Chemical Society, Washington, USA.

The above-described reactions can each be performed under the customary conditions familiar to those skilled in the art, for example with regard to pressure or sequence of addition of the components. It may be possible for the person skilled in the art to determine the optimal process regime under the respective conditions by simple preliminary tests. The intermediate and end products obtained by the reactions described above can each, if desired and/or required, be purified and/or isolated by customary methods known to those skilled in the art. Suitable purification processes are, for example, extraction processes and chromatography processes, such as column chromatography or preparative chromatography. All of the above-described process steps, and in each case also the purification and/or isolation of intermediates or end products, can be performed partly or completely under an inert gas atmosphere, preferably under protective gas atmosphere.

When the inventive substituted compounds of the aforementioned general formula (I) or the compounds 1-15, after preparation thereof, are obtained in the form of a mixture of stereoisomers thereof, preferably in the form of racemates thereof or other mixtures of their different enantiomers and/or diastereomers, these can be separated and possibly isolated by customary processes known to those skilled in the art. Examples include chromatographic separation processes, especially liquid chromatography processes under standard pressure or under elevated pressure, preferably MPLC and HPLC processes, and processes for fractional crystallization. It is possible more particularly to separate individual enantiomers from one another, for example by means of HPLC on a chiral stationary phase, or diastereomeric salts formed by means of crystallization with chiral acids, for instance (+)-tartaric acid, (−)-tartaric acid or (+)-10-camphorsulfonic acid.

EXAMPLE

The target structure (I″) was synthesized by coupling the vinylproline derivatives 6a and 14a and a subsequent ring-closing metathesis to form the characteristic ring system.

The synthesis of the vinylproline derivative 6a was conducted proceeding from L-pyroglutamic acid (1a) in six steps (scheme 3). As an alternative, the synthesis of 6a was developed in five stages proceeding from L-proline (16a) with the aid of an electrochemical oxidation of 17a as the key step (step p). As a further suitable intermediate, compound 6b was synthesized by Cu-catalyzed substitution of the methoxy group in 4a (scheme 3).

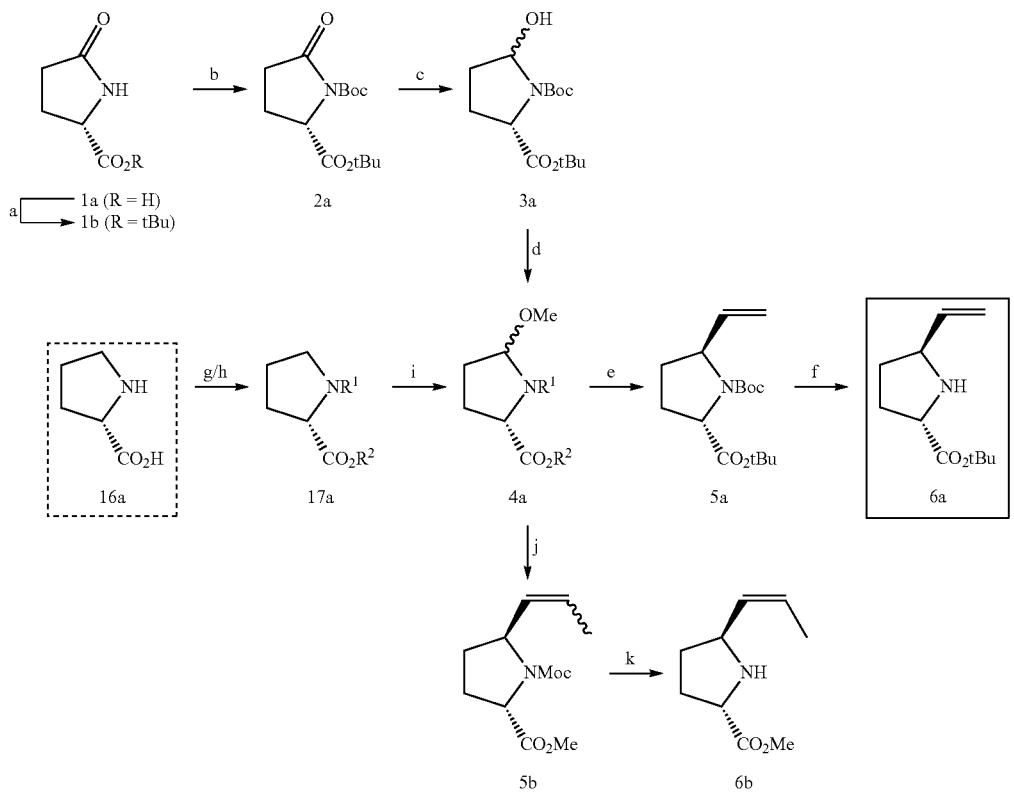

Scheme 3 a) HClO$_4$, tBuOAc, RT, 61%;
b) Boc$_2$O, (NEt$_3$), DMAP, CH$_3$CN, 0° C.-RT, 86%;
c) DIBAL-H, THF, -78° C., 86%;
d) PPTS, MeOH, RT, 85%;
e) 1. CuBrMe$_2$S + Vinyl-MgBr, -50° C. to -40° C., 60 min;
   2. BF$_3$*Et$_2$O -78° C., 15 min, then 10° C. 5 h, Et$_2$O, 60%, trans:cis 3:1 up to 28:1, diastereomer separation
f) TMSOTf, DCM, 0° C., 81%;
g) R$^1$ = Boc, R$^2$ = tBu:
   1. Boc$_2$O, NEt$_3$;
   2. DMAP, tBuOH, RT, 99%;
h) R$^1$ = Moc, R$^2$ = Me: MeOCOCl, NEt$_3$, MeOH, RT, 88%;
i) Bu$_4$NBF$_4$, electrolysis (-2e⁻), MeOH, RT, R$^1$ = Boc, R$_2$ = tBu: 80%, R$^1$ = Moc, R$_2$ = Me: 98%;
j) 1. CuBrMe$_2$S + cis-propenyl-MgBr, -50° C.--40° C., 60 min
   2. BF$_3$*Et$_2$O -78° C., 15 min. warm up to 10° C. over 5 h, Et$_2$O, 57% pure trans-diastereomer
k) TMSI, DCM, RT, 67%.

Proceeding from L-glutamic acid methyl ester hydrochloride (7a), the vinylproline derivative 14a was prepared in seven steps (scheme 4). The key steps were firstly the diastereo selective allylation of 8a to 9a, and the isomerization of the double bond (12a to 12b).

form the 8-membered ring, which was expected to be difficult, was achieved with satisfactory yield (57%), at least when relatively high loadings (30 mol %) of the Grubbs II catalyst were used. However, adhering Ru residues and the associated

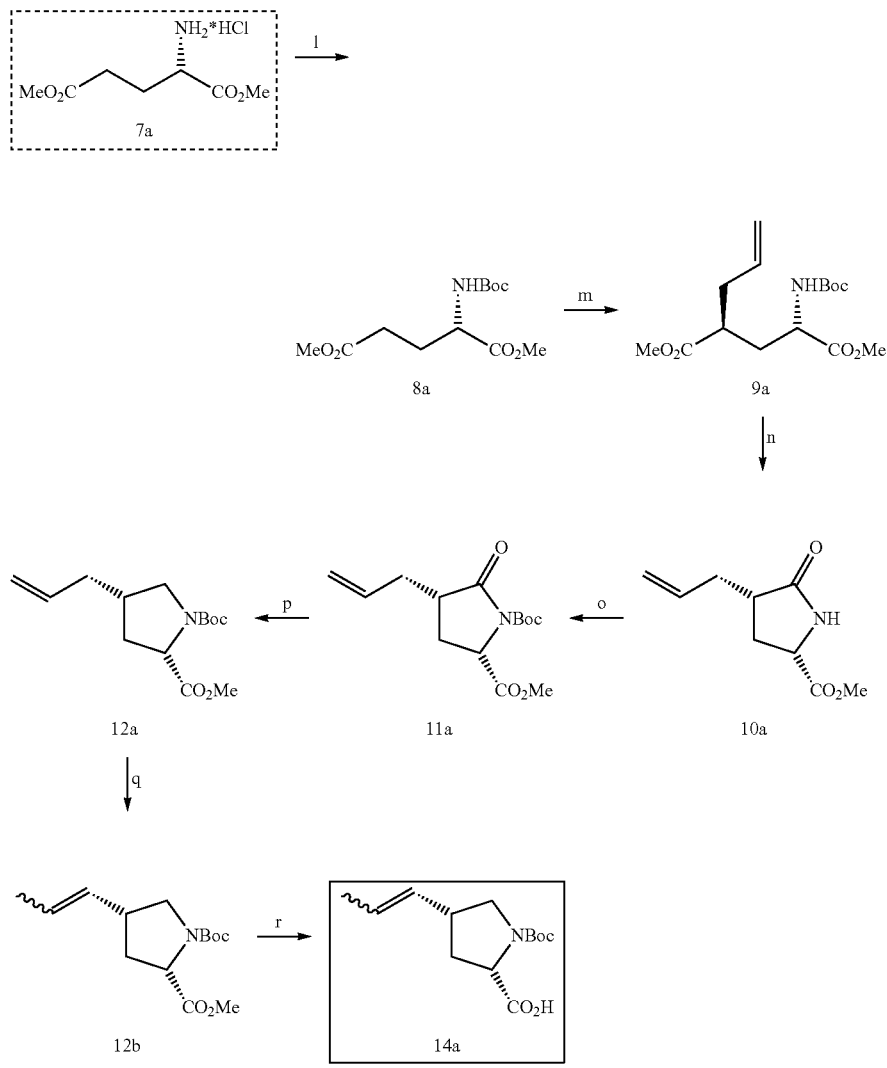

Scheme 4 l) DMAP, (NEt$_3$), Boc$_2$O, DCM, 0° C.-RT, 68%;
m) 1. LiHMDS, THF, -78° C.;
   2. Allyl-Br, THF, -78° C., 80% (syn:anti 1:30);
n) H$_3$PO$_4$, THF, RT, 70-91%;
o) Boc$_2$O, (NEt$_3$), DMAP, DCM, 0° C.-RT, 90%, cis:trans 6:1, diastereomer separation
p) 1. LiEt$_3$BH, THF, -78° C.;
   2. Et$_3$SiH, BF$_3$*Et$_2$O, DCM, -78° C., 78%;
q) 5 mol % [Ir(PPh$_3$)$_{2-3}$Sol$_{1-2}$]SbF$_6$, DCM/acetone 50/1, RT, 50-84%
r) LiOH*H$_2$O, MeOH, H$_2$O, THF, RT, 78 to 99%;

The coupling of the vinylproline derivatives 6a and 14a to the depeptide 15a proceeded with varying yields (20-76%). The subsequent metathesis to give (I'), i.e. the ring closure to instability of the metathesis product (I') caused the actual target product (I") to be obtained to date only in contaminated form (and poor yield) (scheme 5).

Scheme 5

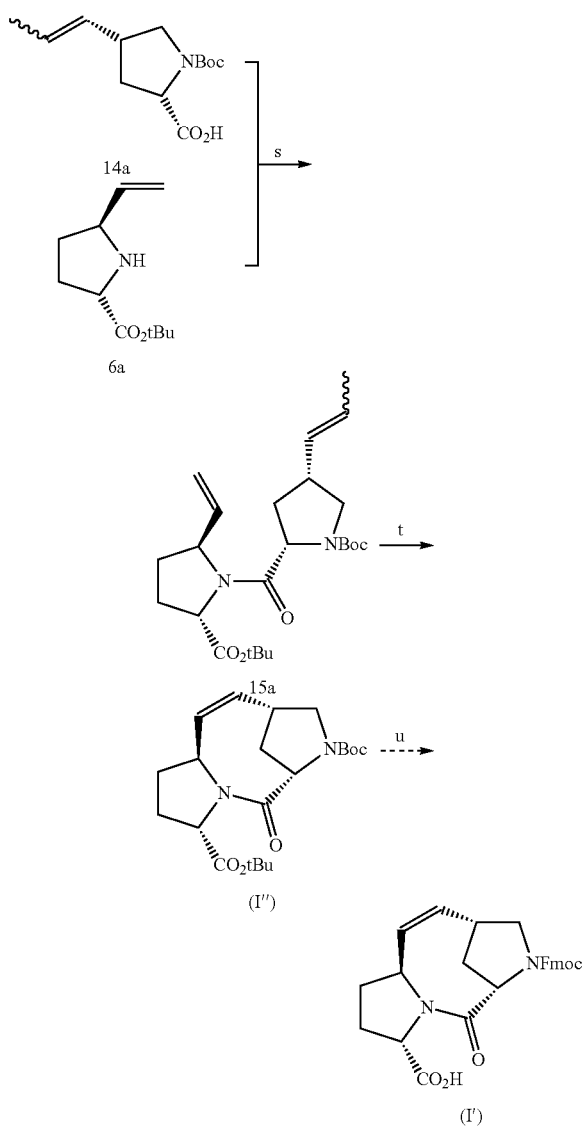

s) DIPEA, PyBOP, MeCN, RT, 20-76%;
t) 30 mol% Grubbs-II, DCM, Δ, 57%;
u) 1. TFA, DCM, 0° C.-RT; 2. $K_2CO_3$, Fmoc-Cl, THF, $H_2O$, RT, 10%.

The invention claimed is:
1. A compound of the formula (I):

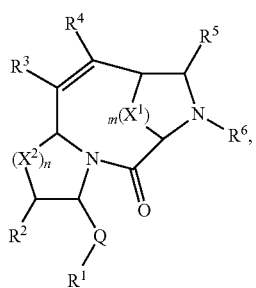

in which
Q is C(=O) or S(=O)$_2$;
$X^1$ and $X^2$ are each independently $CH_2$ or $CHR^7$, where $R^7$ is $C_{1-10}$-alkyl, saturated or unsaturated, branched or unbranched, unsubstituted or mono- or polysubstituted;

m and n are each 1;

$R^1$ is $C_{1-10}$-alkyl, saturated or unsaturated, branched or unbranched, unsubstituted or mono- or polysubstituted; $C_{3-10}$-cycloalkyl or heterocyclyl, each saturated or unsaturated, unsubstituted or mono- or polysubstituted; aryl or heteroaryl, each unsubstituted or mono- or polysubstituted; $C_{1-8}$-alkyl-bridged $C_{3-10}$-cycloalkyl or heterocyclyl, each saturated or unsaturated, unsubstituted or mono- or polysubstituted, where the alkyl chain in each case may be branched or unbranched, saturated or unsaturated, unsubstituted, mono- or polysubstituted; or $C_{1-8}$-alkyl-bridged aryl or heteroaryl, each unsubstituted or mono- or polysubstituted, where the alkyl chain in each case may be branched or unbranched, saturated or unsaturated, unsubstituted, mono- or polysubstituted;
$OR^8$; $NR^8R^9$;
$NHC(=O)R^8$; $NR^8R^9$; or $NH—S(=O)_2R^8$;
where $R^8$ and $R^9$ are each independently H; $C_{1-10}$-alkyl, saturated or unsaturated, branched or unbranched, unsubstituted or mono- or polysubstituted; $C_{3-10}$-cycloalkyl or heterocyclyl, each saturated or unsaturated, unsubstituted or mono- or polysubstituted; aryl or heteroaryl, each unsubstituted or mono- or polysubstituted; $C_{1-8}$-alkyl-bridged $C_{3-10}$-cycloalkyl or heterocyclyl, each saturated or unsaturated, unsubstituted or mono- or polysubstituted, where the alkyl chain in each case may be branched or unbranched, saturated or unsaturated, unsubstituted, mono- or polysubstituted; or $C_{1-8}$-alkyl-bridged aryl or heteroaryl, each unsubstituted or mono- or polysubstituted, where the alkyl chain in each case may be branched or unbranched, saturated or unsaturated, unsubstituted, mono- or polysubstituted;

or $R^1$ is —NHCHR$^a$(=O)—R$^b$ where
$R^a$ is selected from the group consisting of —H, —$CH_3$, —CH(CH$_3$)$_2$, —$CH_2$CH(CH$_3$)$_2$, —CH(CH$_3$)CH$_2$CH$_3$, —CH$_2$CH$_2$SCH$_3$, —CH$_2$C$_6$H$_5$, —CH$_2$-indolyl, —CH$_2$OH, —CH(OH)CH$_3$, —CH$_2$C(=O)NH$_2$, —CH$_2$CH$_2$C(=O)NH$_2$, —CH$_2$—C$_6$H$_4$—OH, —CH$_2$SH, —CH$_2$CH$_2$CH$_2$NH$_2$, —CH$_2$CH$_2$CH$_2$NHC(=NH)NH$_2$, —CH$_2$-imidazolyl, —CH$_2$CO$_2$H, and —CH$_2$CH$_2$CO$_2$H; and
$R^b$ is selected from —OH and -peptidyl, where the peptidyl is bonded covalently via its N terminus;

$R^2$ and $R^5$ are each independently H; $C_{1-10}$-alkyl, saturated or unsaturated, branched or unbranched, unsubstituted or mono- or polysubstituted;
$R^3$ and $R^4$ are each independently H; $C_{1-10}$-alkyl, saturated or unsaturated, branched or unbranched, unsubstituted or mono- or polysubstituted; aryl or heteroaryl, each unsubstituted or mono- or polysubstituted;
$R^6$ is H; $C_{1-10}$-alkyl, saturated or unsaturated, branched or unbranched, unsubstituted or mono- or polysubstituted; $C_{3-10}$-cycloalkyl or heterocyclyl, each saturated or unsaturated, unsubstituted or mono- or polysubstituted; aryl or heteroaryl, each unsubstituted or mono- or polysubstituted; $C_{1-8}$-alkyl-bridged $C_{3-10}$-cycloalkyl or heterocyclyl, each saturated or unsaturated, unsubstituted or mono- or polysubstituted, where the alkyl chain in each case may be branched or unbranched, saturated or unsaturated, unsubstituted, mono- or polysubstituted; or $C_{1-8}$-alkyl-bridged aryl or heteroaryl, each unsubstituted or mono- or polysubstituted, where the alkyl chain in each case may be branched or unbranched, saturated or unsaturated, unsubstituted, mono- or polysubstituted; $C(=O)R^{10}$;
$C(=O)OR^{10}$; $C(=O)NR^{10}R^{11}$; $S(=O)_2-R^{10}$; $S(=O)_2OR^{10}$; or $S(=O)_2NR^{10}R^{11}$;
where $R^{10}$ and $R^{11}$ are each independently H; $C_{1-10}$-alkyl, saturated or unsaturated, branched or unbranched, unsubstituted or mono- or polysubstituted; $C_{3-10}$-cycloalkyl or heterocyclyl, each saturated or unsaturated, unsubstituted or mono- or polysubstituted; aryl or heteroaryl, each unsubstituted or mono- or polysubstituted; $C_{1-8}$-alkyl-bridged $C_{3-10}$-cycloalkyl or heterocyclyl, each saturated or unsaturated, unsubstituted or mono- or polysubstituted, where the alkyl chain in each case may be branched or unbranched, saturated or unsaturated, unsubstituted, mono- or polysubstituted; or $C_{1-8}$-alkyl-bridged aryl or heteroaryl, each unsubstituted or mono- or polysubstituted, where the alkyl chain in each case may be branched or unbranched, saturated or unsaturated, unsubstituted, mono- or polysubstituted;

or $R^6$ is $-C(=O)-CHR^yNHR^z$ where
$R^y$ is selected from the group consisting of $-H$, $-CH_3$, $-CH(CH_3)_2$, $-CH_2CH(CH_3)_2$, $-CH(CH_3)CH_2CH_3$, $-CH_2CH_2SCH_3$, $-CH_2C_6H_5$, $-CH_2$-indolyl, $-CH_2OH$, $-CH(OH)CH_3$, $-CH_2C(=O)NH_2$, $CH_2CH_2C(=O)NH_2$, $-CH_2-C_6H_4-OH$, $-CH_2SH$, $-CH_2CH_2CH_2CH_2NH_2$, $-CH_2CH_2CH_2NHC(=NH)NH_2$, $-CH_2$-imidazolyl, $-CH_2CO_2H$, and $-CH_2CH_2CO_2H$; and
$R^z$ is selected from $-H$ and $-C(=O)-C_{1-8}$-alkyl;

in which "alkyl substituted", "heterocyclyl substituted" and "cycloalkyl substituted" on the corresponding radicals represents the substitution of one or more hydrogen atoms in each case independently by F; Cl; Br; I; $NO_2$; CN; $CF_3$; $C_{1-8}$-alkyl; phenyl; $C(=O)OH$; $C(=O)O-C_{1-8}$-alkyl; $C(=O)O$-phenyl; $C(=O)NH_2$; $C(=O)NH-C_{1-8}$-alkyl; $C(=O)NH$-phenyl; $C(=O)N(C_{1-8}$-alkyl$)_2$; OH; =O; $OCF_3$; $O-C_{1-8}$-alkyl; $O-C(=O)-C_{1-8}$-alkyl; SH; $SCF_3$; $S-C_{1-8}$-alkyl; $S(=O)_2OH$; $S(=O)_2C_{1-8}$-alkyl; $S(=O)_2O-C_{1-8}$-alkyl; $S(=O)_2NH-C_{1-8}$-alkyl; $S(=O)_2N(C_{1-8}$-alkyl$)_2$; $NH_2$; $NH-C_{1-8}$-alkyl; NH-phenyl; $N(C_{1-8}$-alkyl$)_2$; $NH-C(=O)-C_{1-8}$-alkyl; $NH-S(=O)_2-C_{1-8}$-alkyl;

in which "aryl substituted" and "heteroaryl substituted" on the corresponding radicals represents the substitution of one or more hydrogen atoms in each case independently by F; Cl; Br; I; $NO_2$; CN; $CF_3$; $C_{1-8}$-alkyl; phenyl; $C(=O)OH$; $C(=O)O-C_{1-8}$-alkyl; $C(=O)O$-phenyl; $C(=O)NH_2$; $C(=O)NH-C_{1-8}$-alkyl; $C(=O)NH$-phenyl; $C(=O)N(C_{1-8}$-alkyl$)_2$; OH; $OCF_3$; $O-C_{1-8}$-alkyl; $O-C(=O)-C_{1-8}$-alkyl; SH; $SCF_3$; $S-C_{1-8}$-alkyl; $S(=O)_2OH$; $S(=O)_2 C_{1-8}$-alkyl; $S(=O)_2O-C_{1-8}$-alkyl; $S(=O)_2NH-C_{1-8}$-alkyl; $S(=O)_2N(C_{1-8}$-alkyl$)_2$; $NH_2$; $NH-C_{1-8}$-alkyl; NH-phenyl; $N(C_{1-8}$-alkyl$)_2$; $NH-C(=O)-C_{1-8}$-alkyl; $NH-S(=O)_2-C_{1-8}$-alkyl;

in each case in the form of a free compound; of a racemic mixture; of an enantiomer, diastereomer, a mixture of the enantiomers or diastereomers, or of a single enantiomer or diastereomer; or in the form of a salt of a physiologically compatible acid or base.

2. A compound as claimed in claim 1, wherein
$X^1$ and $X^2$ are each $CH_2$; and
m and n are each 1.

3. A compound as claimed in claim 1, wherein
$R^1$ is $OR^8$; $NHR^8$ or $NHC(=O)R^8$;
where $R^8$ is H; $C_{1-10}$-alkyl, saturated or unsaturated, branched or unbranched, unsubstituted or mono- or polysubstituted by one or more substituents each independently selected from the group consisting of F, Cl, Br, I, $C(=O)OH$, $C(=O)OC_{1-4}$-alkyl, $C(=O)C_{1-4}$-alkyl, $C(=O)NH-C_{1-4}$-alkyl, OH, $O-C_{1-4}$-alkyl, =O, $NH_2$, $NHC(=O)C_{1-4}$-alkyl, $NHS(=O)_2C_{1-4}$-alkyl, $S(=O)_2OH$, $S(=O)_2OC_{1-4}$-alkyl and $S(=O)_2C_{1-4}$-alkyl; aryl, unsubstituted or mono- or polysubstituted by one or more substituents each independently selected from the group consisting of F, Cl, Br, I, $C_{1-4}$-alkyl, $C(=O)OH$, $C(=O)OC_{1-4}$-alkyl, $C(=O)C_{1-4}$-alkyl, $C(=O)NH-C_{1-4}$-alkyl, OH, $O-C_{1-4}$-alkyl, $NH_2$, $NHC(=O)C_{1-4}$-alkyl, $NHS(=O)_2C_{1-4}$-alkyl, $S(=O)_2OH$, $S(=O)_2C_{1-4}$-alkyl and $S(=O)_2C_{1-4}$-alkyl; or $C_{1-8}$-alkyl-bridged aryl, unsubstituted or mono- or polysubstituted by one or more substituents each independently selected from the group consisting of F, Cl, Br, I, $C_{1-4}$-alkyl, $C(=O)OH$, $C(=O)OC_{1-4}$-alkyl, $C(=O)C_{1-4}$-alkyl, $C(=O)NH-C_{1-4}$-alkyl, OH, $O-C_{1-4}$-alkyl, $NH_2$, $NHC(=O)C_{1-4}$-alkyl, $NHS(=O)_2C_{1-4}$-alkyl, $S(=O)_2OH$, $S(=O)_2OC_{1-4}$-alkyl and $S(=O)_2C_{1-4}$-alkyl; where the alkyl chain may in each case be branched or unbranched, saturated or unsaturated, unsubstituted;

or $R^1$ is $-NHCHR^aC(=O)-R^b$ where
$R^a$ is selected from the group consisting of $-H$, $-CH_3$, $-CH(CH_3)_2$, $-CH_2CH(CH_3)_2$, $-CH(CH_3)CH_2CH_3$, $-CH_2CH_2SCH_3$, $-CH_2C_6H_5$, $-CH_2$-indolyl, $-CH_2OH$, $-CH(OH)CH_3$, $-CH_2C(=O)NH_2$, $CH_2CH_2C(=O)NH_2$, $-CH_2-C_6H_4-OH$, $-CH_2SH$, $-CH_2CH_2CH_2CH_2NH_2$, $-CH_2CH_2CH_2NHC(=NH)NH_2$, $-CH_2$-imidazolyl, $-CH_2CO_2H$, and $-CH_2CH_2CO_2H$; and
$R^b$ is selected from $-OH$ and -peptidyl, where the peptidyl is bonded covalently via its N terminus.

4. A compound as claimed in claim 1, wherein
$R^2$ and $R^5$ are each independently H; $C_{1-10}$-alkyl, saturated or unsaturated, branched or unbranched, unsubstituted;
$R^3$ and $R^4$ are each independently H; $C_{1-10}$-alkyl, saturated or unsaturated, branched or unbranched, unsubstituted.

5. A compound as claimed in claim 1, wherein
$R^6$ is H; $C_{1-10}$-alkyl, saturated or unsaturated, branched or unbranched, unsubstituted or mono- or polysubstituted by one or more substituents each independently selected from the group consisting of F, Cl, Br, I, $C(=O)OH$, $C(=O)OC_{1-4}$-alkyl, $C(=O)C_{1-4}$-alkyl, $C(=O)NH-C_{1-4}$-alkyl, OH, $O-C_{1-4}$-alkyl, =O, $NH_2$, $NHC(=O)C_{1-4}$-alkyl, $NHS(=O)_2C_{1-4}$-alkyl, $S(=O)_2OH$, $S(=O)_2OC_{1-4}$-alkyl and $S(=O)_2C_{1-4}$-alkyl;

or is $C(=O)R^{10}$; $C(=O)OR^{10}$; $C(=O)NR^{10}R^{11}$; $S(=O)_2-R^{10}$; $S(=O)_2OR^{10}$; or $S(=O)_2NR^{10}R^{11}$,
where $R^{10}$ and $R^{11}$ are each independently H; $C_{1-10}$-alkyl, saturated or unsaturated, branched or unbranched, unsubstituted or mono- or polysubstituted by one or more substituents each independently selected from the group consisting of F, Cl, Br, I, $C_{1-4}$-alkyl $C(=O)OH$, $C(=O)OC_{1-4}$-alkyl, $C(=O)C_{1-4}$-alkyl, $C(=O)NH-C_{1-4}$-alkyl, OH, $O-C_{1-4}$-alkyl, =O, $NH_2$, $NHC(=O)C_{1-4}$-alkyl, $NHS(=O)_2C_{1-4}$-alkyl, $S(=O)_2OH$, $S(=O)_2OC_{1-4}$-alkyl and $S(=O)_2C_{1-4}$-alkyl; aryl or heteroaryl, unsubstituted or mono- or polysubstituted by one or more substituents each independently selected from the group consisting of F, Cl, Br, I, $C_{1-4}$-alkyl, $C(=O)OH$, $C(=O)$ $OC_{1-4}$-alkyl, $C(=O)C_{1-4}$-alkyl, $C(=O)NH-C_{1-4}$- alkyl, OH, $O-C_{1-4}$-alkyl, $NH_2$, $NHC(=O)C_{1-4}$- alkyl, $NHS(=O)_2C_{1-4}$-alkyl, $S(=O)_2OH$, $S(=O)_2$ $OC_{1-4}$-alkyl and $S(=O)_2C_{1-4}$-alkyl; or $C_{1-8}$-alkyl- bridged aryl or heteroaryl, unsubstituted or mono- or polysubstituted by one or more substituents each independently selected from the group consisting of F, Cl, Br, I, $C_{1-4}$-alkyl, $C(=O)OH$, $C(=O)OC_{1-4}$- alkyl, $C(=O)C_{1-4}$-alkyl, $C(=O)NH-C_{1-4}$-alkyl, OH, $O-C_{1-4}$-alkyl, $NH_2$, $NHC(=O)C_{1-4}$-alkyl, $NHS(=O)_2C_{1-4}$-alkyl, $S(=O)_2OH$, $S(=O)_2OC_{1-4}$- alkyl and $S(=O)_2C_{1-4}$-alkyl; where the alkyl chain may in each case be branched or unbranched, saturated or unsaturated, unsubstituted;

or $R^6$ is $-C(=O)-CHR^yNHR^z$ where $R^y$ is selected from the group consisting of $-H$, $-CH_3$, $-CH(CH_3)_2$, $-CH_2CH(CH_3)_2$, $-CH(CH_3)$ $CH_2CH_3$, $-CH_2CH_2SCH_3$, $-CH_2C_6H_5$, $-CH_2$-indolyl, $-CH_2OH$, $-CH(OH)CH_3$, $-CH_2C(=O)$ $NH_2$, $CH_2CH_2C(=O)NH_2$, $-CH_2-C_6H_4-OH$, $-CH_2SH$, $-CH_2CH_2CH_2CH_2NH_2$, $-CH_2CH_2CH_2NHC(=NH)NH_2$, $-CH_2$-imidazolyl, $-CH_2CO_2H$, and $-CH_2CH_2CO_2H$; and $R^z$ is selected from $-H$ and $-C(=O)-C_{1-8}$-alkyl.

6. A compound as claimed in claim 1, wherein
$X^1$ and $X^2$ are each $CH_2$;
m and n are each 1;
$R^1$ is $OR^8$;

where $R^8$ is H; $C_{1-10}$-alkyl, saturated or unsaturated, branched or unbranched, unsubstituted or mono- or polysubstituted by one or more substituents each independently selected from the group consisting of $C(=O)OH$, $C(=O)OC_{1-4}$-alkyl, $C(=O)C_{1-4}$-alkyl, $C(=O)NH-C_{1-4}$-alkyl, OH, $O-C_{1-4}$-alkyl, $=O$, $NH_2$, $NHC(=O)C_{1-4}$-alkyl, $NHS(=O)_2C_{1-4}$-alkyl, $S(=O)_2OH$, $S(=O)_2OC_{1-4}$-alkyl and $S(=O)_2C_{1-4}$- alkyl; or $C_{1-8}$-alkyl-bridged aryl, unsubstituted or mono- or polysubstituted by one or more substituents each independently selected from the group consisting of F, Cl, Br, I, $C_{1-4}$-alkyl, $C(=O)OH$, $C(=O)$ $OC_{1-4}$-alkyl, $C(=O)C_{1-4}$-alkyl, $C(=O)NH-C_{1-4}$- alkyl, OH, $O-C_{1-4}$-alkyl, $NH_2$, $NHC(=O)C_{1-4}$- alkyl, $NHS(=O)_2C_{1-4}$-alkyl, $S(=O)_2OH$, $S(=O)_2$ $OC_{1-4}$-alkyl and $S(=O)_2C_{1-4}$-alkyl; where the alkyl chain may in each case be branched or unbranched, saturated or unsaturated, unsubstituted;

or $R^1$ is $-NHCHR^aC(=O)-R^b$ where $R^a$ is selected from the group consisting of $-H$, $-CH_3$, $-CH(CH_3)_2$, $-CH_2CH(CH_3)_2$, $-CH(CH_3)$ $CH_2CH_3$, $-CH_2CH_2SCH_3$, $-CH_2C_6H_5$, $-CH_2$-indolyl, $-CH_2OH$, $-CH(OH)CH_3$, $-CH_2C(=O)$ $NH_2$, $CH_2CH_2C(=O)NH_2$, $-CH_2-C_6H_4-OH$, $-CH_2SH$, $-CH_2CH_2CH_2CH_2NH_2$, $-CH_2CH_2CH_2NHC(=NH)NH_2$, $-CH_2$-imidazolyl, $-CH_2CO_2H$, and $-CH_2CH_2CO_2H$; and $R^b$ is selected from $-OH$ and -peptidyl, where the peptidyl is bonded covalently via its N terminus;

$R^2$ and $R^5$ are each H;

$R^3$ and $R^4$ are each H;

$R^6$ is H; $C_{1-10}$-alkyl, saturated or unsaturated, branched or unbranched, unsubstituted or mono- or polysubstituted by one or more substituents each independently selected from the group consisting of $C(=O)OH$, $C(=O)OC_{1-4}$- alkyl, $C(=O)C_{1-4}$-alkyl, $C(=O)NH-C_{1-4}$-alkyl, OH, $O-C_{1-4}$-alkyl, $=O$, $NH_2$, $NHC(=O)C_{1-4}$-alkyl and $NHS(=O)_2C_{1-4}$-alkyl;

or is $C(=O)R^{10}$; $C(=O)OR^{10}$; $C(=O)NR^{10}R^{11}$; $S(=O)_2$ $-R^{10}$; $S(=O)_2OR^{10}$; or $S(=O)_2NR^{10}R^{11}$, where $R^{10}$ and $R^{11}$ are each independently H; $C_{1-10}$- alkyl, saturated or unsaturated, branched or unbranched, unsubstituted or mono- or polysubstituted by one or more substituents each independently selected from the group consisting of $C_{1-4}$-alkyl, $C(=O)OH$, $C(=O)OC_{1-4}$-alkyl, $C(=O)C_{1-4}$-alkyl, $C(=O)NH-C_{1-4}$-alkyl, OH, $O-C_{1-4}$-alkyl, $=O$, $NH_2$, $NHC(=O)C_{1-4}$-alkyl, $NHS(=O)_2C_{1-4}$-alkyl, aryl, unsubstituted or mono- or polysubstituted by one or more substituents each independently selected from the group consisting of $C_{1-4}$-alkyl, $C(=O)OH$, $C(=O)OC_{1-4}$-alkyl, $C(=O)C_{1-4}$-alkyl, $C(=O)NH$- $C_{1-4}$-alkyl, OH, $O-C_{1-4}$-alkyl, $NH_2$, $NHC(=O)$ $C_{1-4}$- alkyl, $NHS(=O)_2C_{1-4}$-alkyl; or $C_{1-8}$-alkyl- bridged aryl or heteroaryl, in each case unsubstituted or mono- or polysubstituted by one or more substituents each independently selected from the group consisting of F, Cl, Br, I, $C_{1-4}$-alkyl, $C(=O)OH$, $C(=O)$ $OC_{1-4}$-alkyl, $C(=O)C_{1-4}$-alkyl, $C(=O)NH-C_{1-4}$- alkyl, OH, $O-C_{1-4}$-alkyl, $NH_2$, $NHC(=O)C_{1-4}$- alkyl, $NHS(=O)_2C_{1-4}$-alkyl, where the alkyl chain may in each case be branched or unbranched, saturated or unsaturated, unsubstituted;

or $R^6$ is $-C(=O)-CHR^yNHR^z$ where $R^y$ is selected from the group consisting of $-H$, $-CH_3$, $-CH(CH_3)_2$, $-CH_2CH(CH_3)_2$, $-CH(CH_3)$ $CH_2CH_3$, $-CH_2CH_2SCH_3$, $-CH_2C_6H_5$, $-CH_2$-indolyl, $-CH_2OH$, $-CH(OH)CH_3$, $-CH_2C(=O)$ $NH_2$, $CH_2CH_2C(=O)NH_2$, $-CH_2-C_6H_4-OH$, $-CH_2SH$, $-CH_2CH_2CH_2CH_2NH_2$, $-CH_2CH_2CH_2NHC(=NH)NH_2$, $-CH_2$-imidazolyl, $-CH_2CO_2H$, and $-CH_2CH_2CO_2H$; and $R^z$ is selected from $-H$ and $-C(=O)-C_{1-8}$-alkyl.

7. A pharmaceutical composition comprising at least one compound of the formula (I) as claimed in claim 1
and optionally one or more pharmaceutically acceptable excipients and/or optionally further active ingredients.

* * * * *